US006908924B2

(12) United States Patent
Watanabe et al.

(10) Patent No.: US 6,908,924 B2
(45) Date of Patent: Jun. 21, 2005

(54) N4-ACYLCYTOSINE-1,3-DIOXOLANE NUCLEOSIDES FOR TREATMENT OF VIRAL INFECTIONS

(75) Inventors: Kyoichi A. Watanabe, Stone Mountain, GA (US); Junxing Shi, Duluth, GA (US); Michael J. Otto, Lilburn, GA (US)

(73) Assignee: Pharmasset, Inc., Tucker, GA (US)

( * ) Notice: Subject to any disclaimer, the term of this patent is extended or adjusted under 35 U.S.C. 154(b) by 0 days.

(21) Appl. No.: 10/320,350

(22) Filed: Dec. 16, 2002

(65) Prior Publication Data

US 2003/0176319 A1 Sep. 18, 2003

Related U.S. Application Data

(60) Provisional application No. 60/341,555, filed on Dec. 14, 2001.

(51) Int. Cl.$^7$ .................... C07D 407/04; A61K 31/506; A61P 31/18; A61P 31/22

(52) U.S. Cl. ...................... 514/272; 544/243; 544/320; 544/321

(58) Field of Search ................................ 544/243, 320, 544/321; 514/272

(56) References Cited

U.S. PATENT DOCUMENTS

| 4,522,811 | A | 6/1985 | Eppstein et al. |
| 4,957,924 | A | 9/1990 | Beauchamp |
| 5,561,120 | A | 10/1996 | Lin et al. |
| 5,703,058 | A | 12/1997 | Schinazi et al. |
| 5,905,070 | A | 5/1999 | Schinazi et al. |
| 5,922,867 | A | 7/1999 | Mansour et al. |
| 6,232,300 | B1 | 5/2001 | Schinazi et al. |
| 2003/0013660 | A1 * | 1/2003 | Attardo et al. ................ 514/18 |

FOREIGN PATENT DOCUMENTS

| EP | 99493 | 2/1984 |
| EP | 409 227 A2 | 5/1989 |
| NL | 8901258 | 1/1991 |

OTHER PUBLICATIONS

Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, pp. 451 and 596.*
Kim, Hea O.; Schinazi, Raymond F.; Shanmuganathan, Kirupathevy; Jeong, Lak S.; Beach, J. Warren; Nampalli, Satyanarayana; Cannon, Deborah L.; Chu, Chung K., Journal of Medicinal Chemistry, 36(5), 519–28 (English) 1993.*
Lee, Migyoung; Chu, Chung K.; Pai, S. Balakrishna; Zhu, Yong–Lian; Cheng, Yung–Chi; Chun, Moon Woo; Chung, Won Keun, Bioorganic & Medicinal Chemistry Letters, 5(17), 2011–14 (English) 1995.*

Bacheler LT, Paul M, Otto MJ, Jadhav PK, Stone BA & Miller JA (1994) An assay for HIV RNIn infected cell lysates, and its use for rapid evaluation of antiviral efficacy. Antivir. Chem. Chemother. 5:111–121.
Charvet A–S, Camplo M, Faury P, Graciet JC, Mourier N, Chermann JC & Kraus JL (1994) Inhibition of human immunodeficiency virus type 1 replication by phosphonoformate– and phosphonoacetate–2',3'–dideoxy–3'–thiacytidine conjugates. J. Med. Chem. 37:2216–2223.
Chou T.–C. & Talalay P. Adv. Enzyme Regul. 1984, 22, 27–55.
Glubis et al. (1993) Structure of a dideoxynucleoside active against the HIV (AIDS) virus. Acta Cryst. C49, 1095–1097), $N^4$–acetyl–2',3'–didehydro–2',3'–dideoxy–5–fluorocytidine, and $N^4$–isopropyl–2',3'–didehydro–2',3'–dideoxy–5–fluorocytidine.
Hosteller, K.Y., D.D. Richman, D.A. Carson, L.M. Stuhmiller, G.M. T. van Wijk, and H. van den Bosch, "Greatly enhanced inhibition of human immunodeficiency virus type 1 replication in CEM and HT4–6C cells by 3'–deoxythymidine diphosphate dimyristoylglycerol, a lipid prodrug of 3,–deoxythymidine," Antimicrob. Agents Chemother., 1992, 36, 2025–2029.
Hostetler, K.Y., L.M. Stuhmiller, H.B. Lenting, H. van den Bosch, and D.D. Richman, "Synthesis and antiretroviral activity of phospholipid analogs of azidothymidine and other antiviral nucleosides." J. Biol. Chem., 1990, 265, 61127.
Jadhav PK & MacKay MF (1997) Cyclic urea amide: HIV–1 protease inhibitors with low nanomolar potency against both wild types and protease inhibitor resistant mutants of HIV.J.Med. Chem. 40:181–190).
Kawaguchi et al., Studies on 2',3'–dideoxy–2',3'–didehydropyrimidine nucleosides. II. N4–benzoyl–2',3'–dideoxy–2', 3'–didehydrocytidine as a prodrug of 2',3'–dideoxy–2',3'–didehydrocytidine (DDCN), Chem. Pharm. Bull. (1989), 37(9), 2547–9), $N^4$–benzoyl–2',3'–dideoxycytidine.
Kucera, L.S., N. Iyer, E. Leake, A. Raben, Modest E.K., D.L.W., and C. Piantadosi, "Novel membrane–interactive ether lipid analogs that inhibit infectious HIV–1 production and induce defective virus formation," AIDS Res. Hum. Retroviruses, 1990, 6, 491–501.
Ladner S.K., Otto M.J., Barker C.S., Zaifert K., Wang G.H., Guo J.T., Seeger C. & King R.W. Antimicrob. Agents Chemother. 1997, 41, 1715–1720).

(Continued)

Primary Examiner—Thomas C. McKenzie
(74) Attorney, Agent, or Firm—Sherry M. Knowles, Esq.; King & Spalding, LLP

(57) ABSTRACT

The present invention is directed to a compound, method and composition of treating or preventing viral infections, in particular, human immunodeficiency virus (HIV) and hepatitis B virus (HBV) infections, in human patients or other animal hosts, comprising the administration of $N^4$-acylcytosine-1,3-dioxolane and pharmaceutically acceptable salts, prodrugs, and other derivatives thereof.

34 Claims, No Drawings

OTHER PUBLICATIONS

Mauldin et al. (1998) Synthesis and antiviral activity of prodrugs of the nucleoside 1–[2',3'–dideoxy–3'–C–(hydroxymethyl)–β–D–erythropentofuranosyl] cytosine. Bioorg. Med. Chem. 6, 577–585).

Piantadosi, C., J. Marasco C.J., S.L. Morris–Natschke, K.L. Meyer, F. Gumus, J.R. Surles, K.S. Ishaq, L.S. Kucera, N. Iyer, C.A. Wallen, S. Piantadosi, and E.J. Modest, "Synthesis and evaluation of novel ether lipid nucleoside conjugates for anti–HIV activity," *J. Med. Chem.*, 1991, 34, 1408–1414.

Schinazi R.F., McMillan A., Cannon D., Mathis R., Lloyd R.M. Jr., Peck A., Sommadossi J.–P., St. Clair M., Wilson J., Furman P.A., Painter G., Choi W.–B., Liotta D.C. Antimicrob. Agents Chemother. 1992, 36, 2423.

Schinazi R.F., Sommadossi J.–P., Saalmann V., Cannon D.L., Xie M.–Y., Hart G.C., Smith G.A. & Hahn E.F. *Antimicrob Agents Chemother.* 1990, 34, 1061–1067).

Shi et al. (1999) Synthesis and biological evaluation of 2',3'–didehydro–2',3'–dideoxy–5–fluorocytidine (d4FC) analogues: discovery of carbocyclic nucleoside triphosphates with potent inhibitory activity against HIV–1 reverse transcriptase. J. Med. Chem. 42, 859–867).

\* cited by examiner

N4-ACYLCYTOSINE-1,3-DIOXOLANE NUCLEOSIDES FOR TREATMENT OF VIRAL INFECTIONS

The present application claims priority to U.S. Ser. No. 60/341,555 filed on Dec. 14, 2001.

FIELD OF THE INVENTION

The present invention is directed to compounds, methods and compositions for the treatment or prevention of viral infections using nucleoside analogues. More specifically, the invention describes $N^4$-acyl-substituted cytosine nucleoside analogues, pharmaceutically acceptable salts, prodrugs, or other derivatives thereof, and the use thereof in the treatment of a viral infection, and in particular a human immunodeficiency virus (HIV) or hepatitis B virus (HBV) infection.

BACKGROUND OF THE INVENTION

In 1981, acquired immune deficiency syndrome (AIDS) was identified as a disease that severely compromises the human immune system, and that without exception leads to death. In 1983, the etiological cause of AIDS was determined to be what is now known as human immunodeficiency virus (HIV).

Another virus that causes a serious human health problem is the hepatitis B virus (HBV). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a 2- to 6-month incubation period, during which the host is typically unaware of the infection, HBV infection can lead to acute hepatitis and liver damage, resulting in abdominal pain, jaundice and elevated blood levels of certain enzymes. HBV can cause fulminant hepatitis, a rapidly progressive, often fatal form of the disease in which large sections of the liver are destroyed.

Patients typically recover from the acute phase of HBV infection. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In Western, industrialized countries, the high-risk group for HBV infection includes those in contact with HBV carriers or their blood samples. The epidemiology of HBV is very similar to that of HIV/AIDS, which is a reason why HBV infection is common among patients infected with HIV or suffering from AIDS. However, HBV is more contagious than HIV.

In 1985, it was reported that the synthetic nucleoside 3'-azido-3'-deoxythymidine (AZT) inhibited the replication of HIV. Since then, several other synthetic nucleosides, including but not limited to 2',3'-dideoxyinosine (ddI), 2',3'-dideoxycytidine (ddC), 2',3'-dideoxy-2',3'-didehydrothymidine (d4T), (−)-2',3'-dideoxy-3'-thiacytidine (3TC), and (−)-carbocyclic 2',3'-didehydro-2',3'-dideoxyguanosine (carbovir) and its prodrug abacavir, have proven effective against HIV. After phosphorylation to the 5'-triphosphate by cellular kinases, these synthetic nucleosides are incorporated into a growing strand of viral DNA, causing chain termination, because they lack a 3'-hydroxyl group. Some nucleosides also inhibit the viral enzyme reverse transcriptase.

3TC (lamivudine) and interferon are currently the only FDA-approved drugs for the treatment of HBV infection. Viral resistance develops within 6 months of 3TC treatment in about 14% of patients.

Cis-2-hydroxymethyl-5-(5-fluorocytosin-1-yl)-1,3-oxathiolane (FTC) is currently in clinical trials for the treatment of HIV and separately for HBV by Triangle Pharmaceuticals, Inc. See Schinazi et al. (1992) Selective inhibition of human immunodeficiency viruses by racemates and enantiomers of cis-5-fluoro-1-[2-(hydroxymethyl)-1,3-oxathiolane-5-yl]cytosine. *Antimicrob. Agents Chemother.* 36, 2423–2431; U.S. Pat. Nos. 5,210,085; 5,914,331; 5,814,639; WO 91/11186; and WO 92/14743.

There has also been a signficant amount of research on 1,3-dioxolane nucleosides and their use to treat viral infections. U.S. Pat. Nos. 5,210,085; 5,276,151; 5,852,027; and 5,179,104 disclose 5-fluorocytosine-1,3-dioxolane nucleoside and nucleoside analogues for the treatment of viral infections.

The success of various synthetic nucleosides in inhibiting the replication of HIV in vivo or in vitro has led a number of researchers to design and test nucleosides that substitute a heteroatom for the carbon atom at the 3'-position of the nucleoside. Norbeck, et al., disclosed that (+/−)-1-[(2-β, 4-β)-2-(hydroxymethyl)-4-dioxolanyl]thymine (referred to as (+/−)-dioxolane-T) exhibits a modest activity against HIV ($EC_{50}$ of 20 μM in ATH8 cells), and is not toxic to uninfected control cells at a concentration of 200 μM. Tetrahedron Letters 30 (46), 6246, (1989).

On Apr. 11, 1988, Bernard Belleau, Dilip Dixit, and Nghe Nguyen-Ba at BioChem Pharma filed patent application U.S. Ser. No. 07/179,615 which disclosed a generic group of racemic 2-substituted-4-substituted-1,3-dioxolane nucleosides for the treatment of HIV. The '615 patent application matured into European Patent Publication No. 0 337 713; U.S. Pat. No. 5,041,449; and U.S. Pat. No. 5,270,315 assigned to BioChem Pharma, Inc.

On Dec. 5, 1990, Chung K. Chu and Raymond F. Schinazi filed U.S. Ser. No. 07/622,762, which disclosed an asymmetric process for the preparation of enantiomerically pure β-D-1,3-dioxolane nucleosides via stereospecific synthesis, and certain nucleosides prepared thereby, including (−)-(2R, 4R)-9-[(2-hydroxymethyl)-1,3-dioxolan-4-yl]guanine (DXG), and its use to treat HIV. This patent application issued as U.S. Pat. No. 5,179,104.

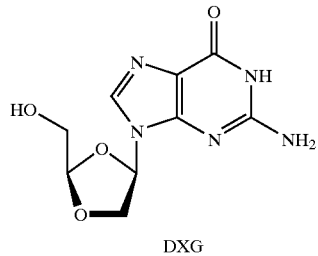

DXG

On May 21, 1991, Tarek Mansour, et al., at BioChem Pharma filed U.S. Ser. No. 07/703,379 directed to a method to obtain the enantiomers of 1,3-dioxolane nucleosides using a stereoselective synthesis that includes condensing a 1,3- dioxolane intermediate covalently bound to a chiral auxiliary with a silyl Lewis acid. The corresponding application filed in Europe was EP 0 515 156.

On Aug. 25, 1992, Chung K. Chu and Raymond F. Schinazi filed U.S. Ser. No. 07/935,515, disclosed certain enantiomerically pure β-D-dioxolanyl purine compounds for the treatment of humans infected with HIV of the formula:

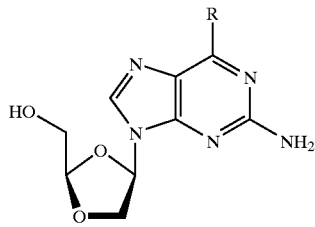

wherein R is OH, Cl, NH$_2$, or H, or a pharmaceutically acceptable salt or derivative of the compounds optionally in a pharmaceutically acceptable carrier or diluent. The compound wherein R is chloro is referred to as (−)-(2R,4R)-2-amino-6-chloro-9-[(2-hydroxymethyl)-1,3-dioxolan-4-yl] purine. The compound wherein R is hydroxy is (−)-(2R,4R)-9-[(2-hydroxy-methyl)-1,3-dioxolan-4-yl]guanine. The compound wherein R is amino is (−)-(2R,4R)-2-amino-9-[(2-hydroxymethyl)-1,3-dioxolan-4-yl]adenine. The compound wherein R is hydrogen is (−)-(2R,4R)-2-amino-9-[(2-hydroxymethyl)-1,3-dioxolan-4yl]purine. This application issued as U.S. Pat. No. 5,925,643.

In 1992, Kim et al., published an asymmetric synthesis for selected 1,3-dioxolane pyrimidine nucleosides from 1,6-anhydro-D-mannose. The specific synthesis resulted in β-D and α-D enantiomers of 1,3-dioxolane nucleosides. Kim et al., 1,3-*Dioxolanylpurine Nucleosides (2R,4R) and (2R,4S) with Selective Anti-HIV-1 Activity in Human Lymphocytes*, J. Med. Chem., 1993 36, 30–37.

In 1992, Belleau et al., at BioChem Pharma, published a method to obtain enantiomerically pure 1,3-dioxolane nucleosides via L-ascorbic acid as a chiral auxiliary in the process. L-ascorbic acid was used to produce a set of diastereomers which could be separated. Belleau, et al., *Oxidative Degradation of L-Ascorbic Acid Acetals to 2',3'-Dideoxy-3'-Oxaribofuranosides Synthesis of Enantiomerically Pure 2',3'-Dideoxy-3'-Oxaribofuranosides. Synthesis of Enantiomerically Pure 2',3'-Dideoxy-3'-Oxacytidine Stereoisomers as Potential Antiviral Agents*. Tetrahedron Lett. 1992, 33:6949.

On Feb. 21, 1992, PCT/US92/01393 (WO 92/14729) by Liotta et al. disclosed a method for the synthesis of 1,3-dioxolane nucleosides that includes condensing a 2-O-protected-5-O-acylated-1,3-dioxolane with a purine of pyrimidine base in the presence of a titanium containing Lewis acid to provide predominately the desired O-isomer in the C1'-position of a 1,3-dioxolane nucleoside. WO 92/14729 also disclosed a process for the resolution of a racemic mixture of 1,3-dioxolane nucleoside enantiomers.

In 1992, Kim et al., published an article teaching how to obtain (−)-L-β-dioxolane-C and (+)-L-β-dioxolane-T from 1,6-anhydro-L-β-glucopyranose. Kim et al., *Potent anti-HIV and anti-HBV Activities of (−)-L-β-Dioxolane-C and (+)-L-β-Dioxolane-T and Their Asymmetric Syntheses*, Tetrahedron Letters Vol 32(46), pp 5899–6902.

On Oct. 28, 1992, Raymond Schinazi filed U.S. Ser. No. 07/967,460 directed to the use of the compounds disclosed in U.S. Ser. No. 07/935,515 for the treatment of hepatitis B. This application has issued as U.S. Pat. Nos. 5,444,063; 5,684,010; 5,834,474; and 5,830,898.

In 1993, Jin et al., at BioChem Pharma published an article that concluded that Lewis acids play a crucial role in the preparation 1,3-dioxolane nucleosides. TiCl$_4$ and SnCl$_4$ promote the formation of dioxolane nucleosides with racemization in the coupling of enantiomerically pure 2'-deoxy-3'-oxaribosides with silylated N-acetylcytosine. The use of the Lewis acids trimethylsilyltriflate, trimethylsilyl iodide, and TiCl$_2$(O-$^i$Pr)$_2$ furnished enantiomerically pure cytosine dioxolane nucleosides in low diastereoselectivity. *Unexpected Effects of Lewis Acids in the Synthesis of Optically Pure 2'-Deoxy-3'-Oxacytidine Nucleoside Analogs*, Tetrahedron Asymmetry vol 4, No. 2 pp 211–214 (1993).

In 1993, Siddiqui, et al., at BioChem and Glaxo published that cis-2,6-diaminopurine dioxolane can be deaminated selectively using adenosine deaminase. Siddiqui, et al., *Antiviral Optically Pure dioxolane Purine Nucleoside Analogues*, Bioorganic & Medicinal Chemistry Letters, Vol. 3 (8), pp 1543–1546 (1993). (−)-(2R,4R)-2-amino-9-[(2-hydroxymethyl)-1,3-dioxolan-4-yl]adenine (DAPD) is a selective inhibitor of HIV-1 replication in vitro as a reverse transcriptase inhibitor (RTI). DAPD is thought to be deaminated in vivo by adenosine deaminase, a ubiquitous enzyme, to yield (−)-β-D-dioxolane guanine (DXG), which is subsequently converted to the corresponding 5'-tri-phosphate (DXG-TP). Biochemical analysis has demonstrated that DXG-TP is a potent inhibitor of the HIV reverse transcriptase (HIV-RT) with a Ki of 0.019 μM.

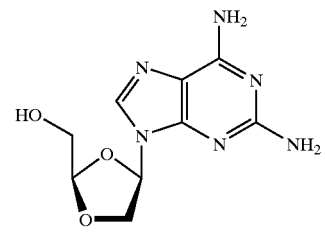

DAPD

Other nucleosides that have been successful in anti-viral treatments include of 2',3'-dideoxy- and 2',3'-didehydro-2,'3'-dideoxy-nucleosides (referred to as a "ddN" or "d2N" nucleoside and a "d4N" nucleoside, respectively), particularly, these nucleosides inhibit the replication of HIV in vivo or in vitro, thus, has led a number of researchers to design and test a variety of modified d2- and d4-nucleosides. One modification has been the replacement of the 5-hydrogen on cytosine nucleosides with fluorine, resulting in several 5-fluorocytosine nucleosides with antiviral activity, including but not limited to β-D- and β-L-2',3'-dideoxy-5-fluorocytine (β-D-D2FC and β-L-D2FC) (U.S. Pat. Nos. 4,788,181 and 6,156,737).

β-D-2',3'-Dideoxy-2',3'-didehydro-5-fluorocytidine (d4FC) and its use to treat hepatitis B was first described in Example 2 of European Pat. Application No. 0 409 227 A2 (Ajinomoto Co., Inc.). Netherlands Pat. No. 8901258 (Stichting Rega V. Z. W.) discloses generally 5-halogeno-2',3'-dideoxy-2',3'-didehydrocytidine derivatives for use in treating HIV and HBV. β-D- and β-L-2',3'-didehydro-2',3'-dideoxy-5-fluorocytidine were further described in U.S. Pat. Nos. 5,703,058; 5,905,070; 6,232,300; and 5,561,120. U.S. Pat. No. 5,703,058 claims a method for the treatment of HIV and/or HBV infection that includes administering an effective amount of β-L-d4FC in combination or alternation with cis-2-hydroxymethyl-5-(5-fluorocytosin-1-yl)-1,3- oxathiolane, cis-2-hydroxymethyl-5-(cytosin-1-yl)-1,3-oxathiolane, 9-[4-(hydroxymethyl)-2-cyclopenten-1-yl)-guanine (carbovir), 9-[(2-hydroxyethoxy)methyl]-guanine (acyclovir), interferon, 3'-deoxy-3'-azido-thymidine (AZT), 2',3'-dideoxyinosine (ddI), 2',3'-dideoxycytidine (ddC), (−)-2'-fluoro-5-methyl-β-L-ara-uridine (L-FMAU) or 2',3'-didehydro-2',3'-dideoxythymidine (d4T). U.S. Pat. No. 5,905,070 claims a method for the treatment of HIV and HBV infection that includes administering an effective amount of β-D-d4FC in combination or alternation with cis-2-hydroxymethyl-5-(5-fluorocytosin-1-yl)-1,3-oxathiolane, cis-2-hydroxymethyl-5-(cytosin-1-yl)-1,3-oxathiolane, 9-[4-(hydroxy-methyl)-2-cyclopenten-1-yl)-guanine (carbovir), 9-[(2-hydroxyethoxy)methyl]guanine (acyclovir), interferon, 3'-deoxy-3'-azido-thymidine (AZT), 2',3'-dideoxyinosine (ddI), 2',3'-dideoxycytidine (ddC), (−)-2'-fluoro-5-methyl-β-L-ara-uridine (L-FMAU) or 2',3'-didehydro-2',3'-dideoxythymidine (d4T). U.S. Pat. No. 6,232,300 claims a method to treat HIV with β-D-d4FC.

Modification of the amino group of antiviral cytosine nucleosides has not been fully explored. Only a few $N^4$-substituted cytosine 2',3'-dideoxy nucleosides and $N^4$-substituted cytosine 2',3'-didehydro-2',3'-dideoxy nucleosides have been reported. These include $N^4$-benzoyl-2',3'-didehydro-2,'3-dideoxycytidine (Kawaguchi et al., Studies on 2',3'-dideoxy-2',3'-didehydropyrimidine nucleosides. II. N4-benzoyl-2',3'-dideoxy-2',3'-didehydrocytidine as a prodrug of 2',3'-dideoxy-2',3'-didehydrocytidine (DDCN), Chem. Pharm. Bull. (1989), 37(9), 2547–9), $N^4$-benzoyl-2',3'-dideoxycytidine (Gulbis et al. (1993) Structure of a dideoxynucleoside active against the HIV (AIDS) virus. Acta Cryst. C49, 1095–1097), $N^4$-acetyl-2', 3'-didehydro-2',3'-dideoxy-5-fluorocytidine, and $N^4$-isopropyl-2',3'-didehydro-2',3'-dideoxy-5-fluorocytidine (Shi et al. (1999)) Synthesis and biological evaluation of 2',3'-didehydro-2',3'-dideoxy-5-fluorocytidine (d4FC) analogues: discovery of carbocyclic nucleoside triphosphates with potent inhibitory activity against HIV-1 reverse transcriptase. J. Med. Chem. 42, 859–867). Of the sugar-modified cytosine nucleosides, some $N^4$-acyl and imine-substituted 2',3'-dideoxy-3'-C-hydroxymethylcytidine analogues have been synthesized (Mauldin et al. (1998) Synthesis and antiviral activity of prodrugs of the nucleoside 1-[2',3'-dideoxy-3'-C-(hydroxymethyl)-β-D-erythropentofuranosyl] cytosine. Bioorg. Med. Chem. 6, 577–585), and some $N^4$-acetyl- and phosphonoacetyl-2',3'-dideoxy-3'-thiacytidine nucleosides have been prepared (Charvet et al. (1993) Inhibition of human immunodeficiency virus type 1 replication by phosphonoformate- and phosphonoacetate-2',3'-dideoxy-3'-thiacytidine conjugates. J. Med. Chem. 37, 2216–2223).

Therefore, it is an object of the present invention to provide a compound, method and composition for the treatment or prevention of HIV infection in human patients.

It is another object of the present invention to provide a compound, method and composition for the treatment or prevention of HBV infection in human patients or other host animals.

It is still another object of the present invention to provide a compound, method and composition for the treatment or prevention of HIV and HBV infection in human patients or other host animals.

SUMMARY OF THE INVENTION

It has been found that certain $N^4$-acyl-cytosine 1,3-dioxolane nucleosides, and in particular, $N^4$-acyl-5-fluorocytidine-1,3-dioxolane, show improved inhibitory activity against HIV and HBV. Therefore, a method for the treatment or prevention of HIV and/or HBV infection in a host, and in particular, a human, is provided that includes administering an effective amount of a $N^4$-acyl-cytosine nucleoside.

In one embodiment of the present invention, the active compound is of formula (A):

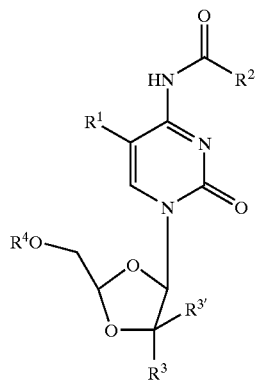

wherein $R^1$ is chosen from hydrogen, halogen (F, Cl, Br, I), alkyl, haloalkyl, alkenyl, haloalkenyl, alkynyl, haloalkynyl, cycloalkyl, CN, $CF_3$, $N_3$, $NO_2$, aryl, heteroaryl and acyl;

$R^3$ and $R^{3'}$ are chosen independently from H, halogen (F, Cl, Br, I), CN, $CF_3$, $N_3$, $NO_2$, alkyl, alkenyl, and alkynyl;

$R^4$ is H, phosphate (including but not limited to monophosphate, diphosphate, triphosphate, or a stabilized phosphate prodrug), carbonyl substituted with alkyl, alkenyl, alkynyl, aryl, or other pharmaceutically acceptable leaving group, which, when administered in vivo, is capable of providing a compound wherein $R^3$ and $R^{3'}$ are H or phosphate, sulfonate ester (including but not limited to alkyl or arylalkyl sulfonyl including but not limited to methanesulfonyl), benzyl (wherein the phenyl group is optionally substituted with one or more substituents as described in the definition or aryl given above), a lipid (including but not limited to a phospholipid), an amino acid, a peptide, or cholesterol; and $R^2$ is chosen from alkyl, alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen (F, Cl, Br, I), CN, $CF_3$, $N_3$, $NO_2$, alkyl, haloalkyl, aminoalkyl, alkoxy, thioalkyl, alkenyl, alkynyl, and aryl.

The compound of the present invention can be in the form of the isolated β-L- or β-D-configuration, or a mixture thereof, including but not limited to a racemic mixture.

In addition, the $N^4$-acylcytosine-1,3-dioxolane nucleosides are inhibitors of HBV. Therefore, these compounds can also be used to treat patients that are co-infected with both HIV and HBV.

The present invention provides a compound, method and composition for treating an HIV infection in a host comprising administering a therapeutically effective amount of at least one compound as described in the present application.

The present invention provides a compound, method and composition for preventing an HIV infection in a host comprising administering a therapeutically effective amount of at least one compound as described in the present application.

The present invention provides a compound, method and composition for treating an HBV infection in a host comprising administering a therapeutically effective amount of at least one compound as described in the present application.

The present invention provides a compound, method and composition for preventing an HBV infection in a host comprising administering a therapeutically effective amount of at least one compound as described in the present application.

The present invention provides a use of a compound for the treatment of HIV and/or HBV infection in a host comprising administering a therapeutically effective amount of at least one compound as described in the present application.

The present invention provides a method of manufacture for a therapeutically effective compound for the treatment of an HIV and/or HBV infection.

In another aspect, there is provided a pharmaceutical formulation comprising a compound of the invention in combination with a pharmaceutically acceptable carrier or excipient for the treatment of a host infected with HIV or HBV.

In still another aspect, there is provided a compound, method and composition for treating or preventing an HIV infection in a host comprising administering to the subject a combination comprising at least one compound of the invention and at least one further therapeutic agent.

In still another aspect, there is provided a method and composition for treating or preventing an HBV infection in a host comprising administering to the subject a combination comprising at least one compound of the invention and at least one further therapeutic agent.

DETAILED DESCRIPTION OF THE INVENTION

It has been found that $N^4$-acyl-cytosine-1,3-dixolane nucleosides, and in particular, $N^4$-acyl-5-fluorocytidine-1,3-dioxolane, show improved inhibitory activity against HIV and HBV. Therefore, a method for the treatment or prevention of a host, and in particular, a human, infected with HIV and/or HBV, is provided that includes administering an effective amount of an $N^4$-acyl-cytosine-1,3-dioxolane nucleosides.

The present invention also provides a compound, method and composition for treating an HIV infection in a host comprising administering a therapeutically effective amount of at least one compound as described in the present application.

The present invention provides a compound, method and composition for preventing an HIV infection in a host comprising administering a therapeutically effective amount of at least one compound as described in the present application.

The present invention provides a compound, method and composition for treating an HBV infection in a host comprising administering a therapeutically effective amount of at least one compound as described in the present application.

The present invention provides a compound, method and composition for preventing an HBV infection in a host comprising administering a therapeutically effective amount of at least one compound as described in the present application.

In another aspect, there is provided a pharmaceutical formulation comprising a compound of the invention in combination with a pharmaceutically acceptable carrier or excipient.

In still another aspect, there is provided a method and composition for treating or preventing an HIV infection in a host comprising administering to the subject a combination comprising at least one compound of the invention and at least one further therapeutic agent.

In still another aspect, there is provided a method and composition for treating or preventing an HBV infection in a host comprising administering to the subject a combination comprising at least one compound of the invention and at least one further therapeutic agent.

I. Active Compound

In one embodiment of the present invention, the active compound is of formula (A):

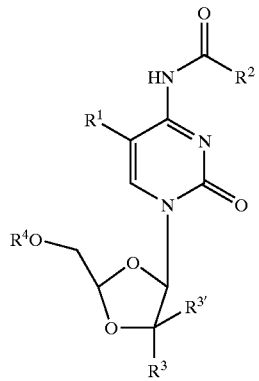

wherein $R^1$ is chosen from hydrogen, halogen (F, Cl, Br, I), alkyl, haloalkyl, alkenyl, haloalkenyl, alkynyl, haloalkynyl, cycloalkyl, CN, $CF_3$, $N_3$, $NO_2$, aryl, heteroaryl and acyl;

$R^3$ and $R^{3'}$ are chosen independently from H, halogen (F, Cl, Br, I), CN, $CF_3$, $N_3$, $NO_2$, alkyl, alkenyl, and alkynyl;

$R^4$ is H, phosphate (including but not limited to monophosphate, diphosphate, triphosphate, or a stabilized phosphate prodrug), carbonyl substituted with alkyl, alkenyl, alkynyl, aryl, or other pharmaceutically acceptable leaving group, which, when administered in vivo, is capable of providing a compound wherein $R^3$ and $R^{3'}$ are H or phosphate, sulfonate ester (including but not limited to alkyl or arylalkyl sulfonyl including but not limited to methanesulfonyl), benzyl (wherein the phenyl group is optionally substituted with one or more substituents as described in the definition or aryl given above), a lipid (including but not limited to a phospholipid), an amino acid, a peptide, or cholesterol; and $R^2$ is chosen from alkyl, alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen (F, Cl, Br, I), CN, $CF_3$, $N_3$, $NO_2$, alkyl, haloalkyl, aminoalkyl, alkoxy, thioalkyl, alkenyl, alkynyl, and aryl.

The compound of the present invention can be in the form of the isolated β-L- or β-D-configuration, or a mixture thereof, including but not limited to a racemic mixture.

In one embodiment of the present invention, the active compound is β-D-$N^4$-p-iodobenzoyl-5-fluorocytidine-1,3-dioxolane, β-D-$N^4$-p-fluoro-benzoyl-5-fluorocytidine-1,3-dioxolane, β-D-$N^4$-p-chlorobenzoyl-5-fluoro-cytidine-1,3-dioxolane, β-D-$N^4$-p-bromobenzoyl-5-fluorocytidine-1,3-dioxolane, β-D-$N^4$-p-ethyl-benzoyl-5-fluorocytidine-1,3-dioxolane, and β-D-$N^4$-p-t-butylbenzoyl-5-fluoro-cytidine-1,3-dioxolane.

In one embodiment of the present invention, the active compound is of formula (A), its pharmaceutically acceptable salt or prodrugs thereof, wherein:
i) $R^4$ is hydrogen;
ii) $R^1$ is fluorine or hydrogen;

iii) $R^3$ and $R^{3'}$ are independently hydrogen or fluorine; and
iv) $R^2$ is a phenyl moiety optionally substituted with halogen (F, Cl, Br, I), CN, $CF_3$, $N_3$, $NO_2$, alkyl, haloalkyl, aminoalkyl, alkoxy, thioalkyl, alkenyl, alkynyl, or aryl in the ortho position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with halogen (F, Cl, Br, I) in the ortho position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Br in the ortho position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with I in the ortho position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with F in the ortho position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Cl in the ortho position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $NO_2$ in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with methyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with ethyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-propyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-propyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-butyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with sec-butyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with tert-butyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-pentyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-pentyl in the ortho position.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with neopentyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with cyclopentyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-hexyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with a cyclohexyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with CN in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $CF_3$ in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $N_3$ in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with haloalkyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with aminoalkyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkoxy in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thioalkyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkenyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkynyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) R3 and R3' are independently hydrogen or fluorine; and
iv) $R^2$ is a phenyl moiety optionally substituted with aryl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with benzyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thiophenyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with furanyl in the ortho position.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with naphthyl in the ortho position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with benzoyl in the ortho position.

In one embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with halogen (F, Cl, Br, I), CN, $CF_3$, $N_3$, $NO_2$, alkyl, haloalkyl, aminoalkyl, alkoxy, thioalkyl, alkenyl, alkynyl, or aryl in the meta position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with halogen (F, Cl, Br, I) in the meta position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Br in the meta position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with I in the meta position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with F in the meta position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Cl in the meta position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $NO_2$ in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with methyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with ethyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-propyl in the meta position.

In yet another embodiment of the present invention, the active compound is of formula, its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-propyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-butyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with sec-butyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with tert-butyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-pentyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-pentyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with neo-pentyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with cyclo-pentyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-hexyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with a cyclohexyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with CN in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $CF_3$ in the meta position.

In yet another embodiment of the present invention, the active compound is of formula (A); its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $N_3$ in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with haloalkyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with aminoalkyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkoxy in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thioalkyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkenyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkynyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with aryl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and iv) $R^2$ is a phenyl moiety optionally substituted with benzyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thiophenyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with furanyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with naphthyl in the meta position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with benzoyl in the meta position.

In one embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with halogen (F, Cl, Br, I), CN, $CF_3$, $N_3$, $NO_2$, alkyl, haloalkyl, aminoalkyl, alkoxy, thioalkyl, alkenyl, alkynyl, or aryl in the para position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with halogen (F, Cl, Br, I) in the para position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Br in the para position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with I in the para position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with F in the para position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with Cl in the para position.

In yet another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $NO_2$ in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with methyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with ethyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-propyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-propyl in the para position.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-butyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with sec-butyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with tert-butyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-pentyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with iso-pentyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with neo-pentyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with cyclo-pentyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with n-hexyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with a cyclohexyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a. phenyl moiety optionally substituted with CN in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $CF_3$ in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with $N_3$ in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with haloalkyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with aminoalkyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkoxy in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thioalkyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkenyl in the para position.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with alkynyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with aryl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with benzyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with thiophenyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with furanyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with naphthyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with benzoyl in the para position.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,6-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,5-dihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4-trihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,5-trihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,5-trihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,6-trihalo.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5,6-trihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4,5-trihalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4,5-tetrahalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4,5,6-pentahalo.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,6-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,5-dialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,5-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,5-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,6-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5,6-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4,5-trialkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4,5-tetraalkyl.

In yet another embodiment of the present invention, the active compound is of formula (A), its pharmaceutically acceptable salts or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4,5,6-pentaalkyl.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,6-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,5-di-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,4-tri-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,3,5-tri-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,5-tri-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,4,6-tri-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 2,5,6-tri-$NO_2$.

In yet another embodiment of the present invention, the active compound is of formula (A), its pharmaceutically acceptable salts or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a phenyl moiety optionally substituted with 3,4,5-tri-$NO_2$.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a thienyl moiety optionally substituted with alkyl, halo, alkenyl, alkynyl, cycloalkyl, aminoalkyl, hydroxyalkyl, haloalkyl, thioalkyl, aryl, or heteroaryl in the 2-position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a thienyl moiety optionally substituted with alkyl, halo, alkenyl, alkynyl, cycloalkyl, aminoalkyl, hydroxyalkyl, haloalkyl, thioalkyl, aryl, or heteroaryl in the 3-position or the 4-position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a benzothiophenyl optionally substituted with alkyl, halo, alkenyl, alkynyl, cycloalkyl, aminoalkyl, hydroxyalkyl, haloalkyl, thioalkyl, aryl, or heteroaryl on the benzene ring.

In another embodiment of the present invention, the active compound is of formula (A), its pharmaceutically acceptable salt or prodrugs thereof, wherein:

i) $R^4$ is hydrogen;
ii) $R^1$ is fluorine or hydrogen;
iii) $R^3$ and $R^{3'}$ are independently hydrogen or fluorine; and
iv) $R^2$ is a benzothiophenyl moiety optionally substituted with alkyl, halo, alkenyl, alkynyl, cycloalkyl, aminoalkyl, hydroxyalkyl, haloalkyl, thioalkyl, aryl, or heteroaryl on the thienyl ring.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a cyclohexyl optionally substituted with alkyl, halo, alkenyl, alkynyl, cycloalkyl, aminoalkyl, hydroxyalkyl, haloalkyl, thioalkyl, aryl, or heteroaryl in the 2 or 3-position.

In another embodiment of the present invention, the active compound is of formula (A), its pharmaceutically acceptable salt or prodrugs thereof, wherein:
i) $R^4$ is hydrogen;
ii) $R^1$ is fluorine or hydrogen;
iii) $R^3$ and $R^{3'}$ are independently hydrogen or fluorine; and
iv) $R^2$ is a cyclohexyl moiety optionally substituted with alkyl, halo, alkenyl, alkynyl, cycloalkyl, aminoalkyl, hydroxyalkyl, haloalkyl, thioalkyl, aryl, or heteroaryl in the 4-position.

In one preferred embodiment, the active compound is β-D-5-fluoro-$N^4$-(4-iodobenzoyl)cytidine-1,3-dioxolane of the structure:

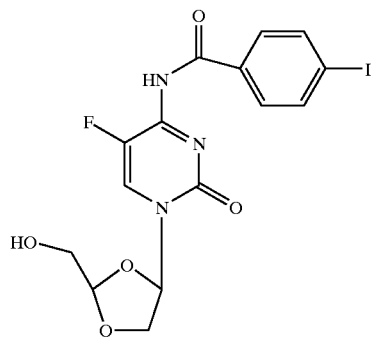

or a pharmaceutically acceptable salt or prodrug thereof.

In another preferred embodiment, the active compound is β-D-5-fluoro-$N^4$-(4-fluorobenzoyl)cytidine-1,3-dioxolane of the structure:

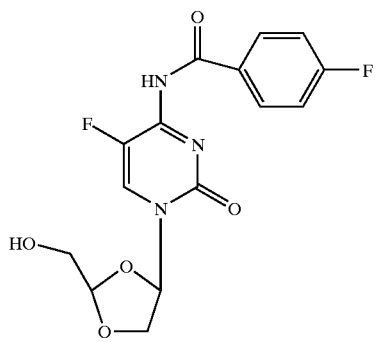

or a pharmaceutically acceptable salt or prodrug thereof.

In still another preferred embodiment, the active compound is β-D-$N^4$-(4-chlorobenzoyl)-5-fluorocytidine-1,3-dioxolane of the structure:

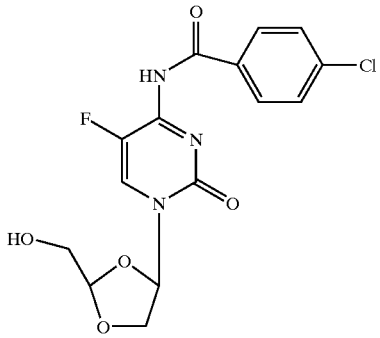

or a pharmaceutically acceptable salt or prodrug thereof.

In one preferred embodiment, the active compound is β-D-$N^4$-(4-bromobenzoyl)-5-fluorocytidine-1,3-dioxolane of the structure:

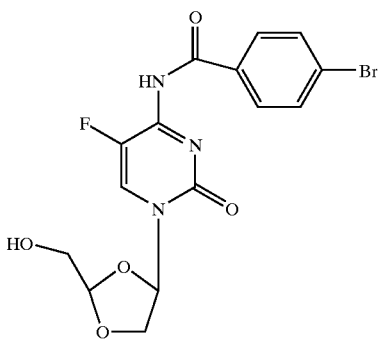

or a pharmaceutically acceptable salt or prodrug thereof.

In another preferred embodiment, the active compound is β-D-5-fluoro-$N^4$-(3-fluorobenzoyl)cytidine-1,3-dioxolane of the structure:

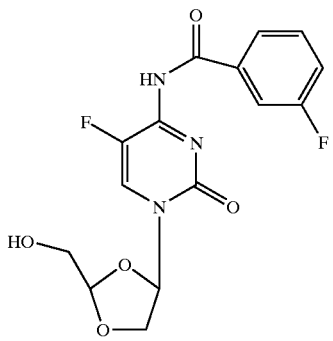

or a pharmaceutically acceptable salt or prodrug thereof.

In still another preferred embodiment, the active compound is β-D-$N^4$-(3-chlorobenzoyl)-5-fluorocytidine-1,3-dioxolane of the structure:

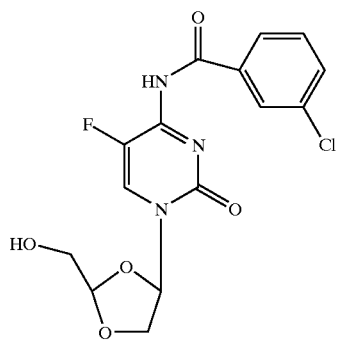

or a pharmaceutically acceptable salt or prodrug thereof.

In one preferred embodiment, the active compound is β-D-N$^4$-(3-bromobenzoyl)-5-fluorocytidine-1,3-dioxolane of the structure:

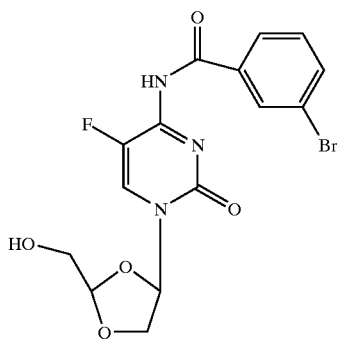

or a pharmaceutically acceptable salt or prodrug thereof.

In another preferred embodiment, the active compound is β-D-5-fluoro-N$^4$-(4-nitrobenzoyl)cytidine-1,3-dioxolane of the structure:

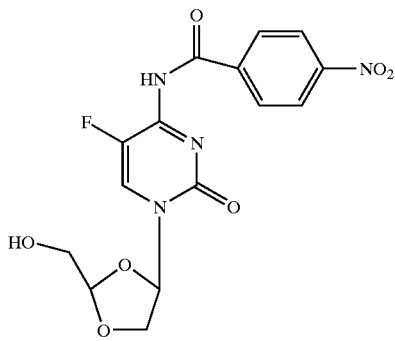

or a pharmaceutically acceptable salt or prodrug thereof.

In still another preferred embodiment, the active compound is β-D-5-fluoro-N$^4$-p-toluoylcytidine-1,3-dioxolane of the structure:

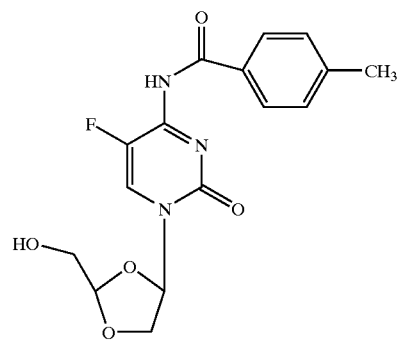

or a pharmaceutically acceptable salt or prodrug thereof.

In one preferred embodiment, the active compound is β-D-5-fluoro-N$^4$-(m-toluoyl)cytidine-1,3-dioxolane of the structure:

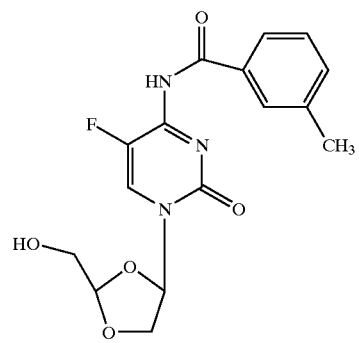

or a pharmaceutically acceptable salt or prodrug thereof.

In another preferred embodiment, the active compound is β-D-N$^4$-(4-ethylbenzoyl)-5-fluorocytidine-1,3-dioxolane of the structure:

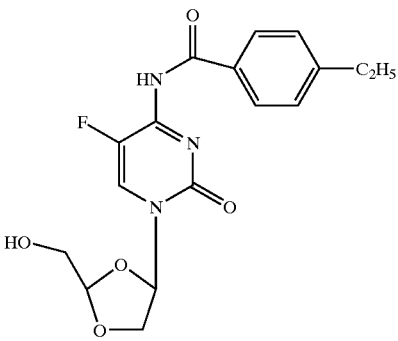

or a pharmaceutically acceptable salt or prodrug thereof.

In still another preferred embodiment, the active compound is β-D-5-fluoro-N$^4$-(4-propylbenzoyl)cytidine-1,3-dioxolane of the structure:

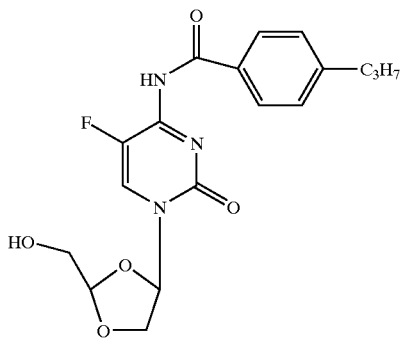

or a pharmaceutically acceptable salt or prodrug thereof.

In one preferred embodiment, the active compound is β-D-N⁴-(4-tert-butylbenzoyl)-5-fluorocytidine-1,3-dioxolane of the structure:

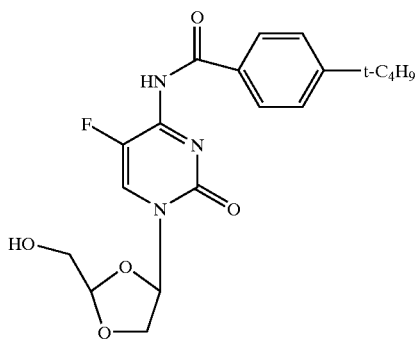

or a pharmaceutically acceptable salt or prodrug thereof.

In still another preferred embodiment, the active compound is β-D-5-fluoro-N⁴-(2-thiophenecarbonyl)cytidine-1,3-dioxolane of the structure:

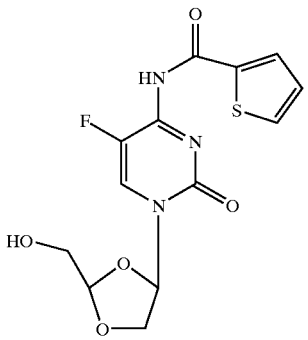

or a pharmaceutically acceptable salt or prodrug thereof.

In one preferred embodiment, the active compound is β-D-N⁴-(benzo-[b]-thiophene-2-carbonyl)-5-fluorocytidine-1,3-dioxolane of the structure:

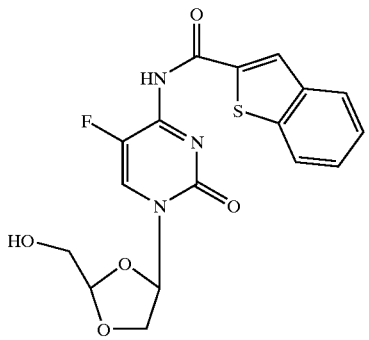

or a pharmaceutically acceptable salt or prodrug thereof.

In another preferred embodiment, the active compound is β-D-N⁴-(cyclohexane-carbonyl)-5-fluorocytidine-1,3-dioxolane of the structure:

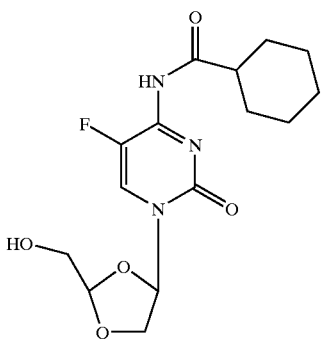

or a pharmaceutically acceptable salt or prodrug thereof.

II. Stereoisomerism and Polymorphism

The compounds of the present invention have asymmetric centers and occur as racemates, racemic mixtures, individual diastereomers or enantiomers, with all isomeric forms being included in the present invention. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

III. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "substantially free of" or "substantially in the absence of" refers to a nucleoside composition that includes at least 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "alkyl," as used herein, unless otherwise specified, refers to a saturated straight, branched, or cyclic, primary, secondary, or tertiary hydrocarbon. The term includes both substituted and unsubstituted alkyl groups. The alkyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

Alkyl groups include, but are not limited to the radicals of methane, ethane, propane, cyclopropane, 2-methylpropane (isobutane), n-butane, 2,2-dimethylpropane (neopentane), cytobutane, 1,1 dimethylcyclopropane, 2-methylbutane, trans-1,2-dimethylcyclopropane, ethylcyclopropane, n-pentane, methylcyclobutane, cis-1,2-dimethylcyclopropane, spiropentane, cyclopentane, 2,2-dimethylbutane, 1,1,2-trimethylcyclopropane, 2,3-dimethylbutane, 2-methylpentane, 3-methylpentane, 1,2,3-trimethylcyclopropane, n-hexane, ethylcyclobutane, methylcyclopentane, 2,2dimethylpentane, 2,4-dimethylpentane, cyclohexane, 2,2,3-trimethylbutane, 3,3-dimethylpentane, 1,1-dimethylcyclopentane, 2,3-dimethylpentane, 2-methylhexane, trans-1,3-dimethylcyclopentane, cis-1,3-dimethylcyclopentane, 3-methylhexane, trans-1,2-dimethylcyclopentane, 3-ethylpentane, quadricyclane (quadricyclo[2,2,1,0$^{2,6}$,o$^{3,5}$] heptane), n-heptane, 2,2,4-trimethylpentane, cis-1,2-dimethylcyclopentane, methylcyclohexane, ethylcyclopentane, 1,1,3-trimethylcyclopentane, 2,2-dimethylhexane, 2,5-dimethylhexane, 1,trans-2, cis-4trimethylcyclopentane, 2,4-dimethylhexane, 2,2,3-trimethylpentane, 1,trans-2,cis-3-trimethylcyclopentane, 3,3-dimethylhexane, 2,3,4-trimethylpentane, 1,1,2-trimethylcyclopentane, 2,3,3-trimethylpentane, 2,3-dimethylhexane, 3-ethyl-2-methylpentane, 1,cis-2,trans-4- trimethylcyclopentane, 1,cis-2,trans-3trimethylcyclopentane, 2-methylheptane, 4-methylheptane, 3,4-dimethylhexane, 1,cis-2,cis-4trimethylcyclopentane, 3-ethyl-3-methylpentane, 3-ethylhexane, 3-methylheptane, cyloheptane (suberane), trans-1,4-dimethylcyclohexane, 1,1-dimethylcyclohexane, cis-1,3-dimethylcychohexane, trans-1-ethyl-3-methylcyclopentane, trans-1-ethyl-2-methylcyclopentane, cis-1-ethyl-3-methylcyclopentane, 1-ethyl-1-methylcyclopentane, 2,2,4,4-tetramethylpentane, 1,cis-2-cis-3-trimethylcyclopentane, trans-1,2-dimethylcyclohexane, 2,2,5-trimethylhexane, trans-1,3-dimethylcyclohexane, n-octane, isopropylcyclopentane, 2,2,4-trimethylhexane, cis-1-ethyl-2-methylcyclopentane, cis-1,2-dimethylcyclohexane, 2,4,4-trimethylhexane, n-propylcyclopentane, 2,3,5-trimethylhexane, ethylcyclohexane, 2,2-dimethylheptane, 2,2,3,4-tetramethylpentane, 2,4-dimethylheptane, methylcycloheptane, 2,2,3-trimethylhexane, 4-ethyl-2-methylhexane, 3-ethyl-2.2-dimethylpentane, 4,4-dimethylheptane, 2,6-dimethylheptane, 2,5-dimethylheptane, 3,5-dimethylheptane, bicyclo[4.2.0]octane, cis-bicyclo[3.3.0]octane, 2,4-dimethyl-3-ethylpentane, 1,1,3-trimethylcyclohexane, 3,3-dimethylheptane, 2,2,5,5-tetramethylhexane, 2,3,3-trimethylhexane, 3-ethyl-2-methylhexane, trans-1,3,5-trimethylcyclohexane, 2,3,4-trimethylhexane, cis-1,3,5-trimethylcyclohexane, trans-1,2,4-trimethylcyclohexane, 2,2,3,3-tetramethylpentane, 4-ethyl-3-methylhexane, 3,3,4-trimethylhexane, 2,3-dimethylheptane, 3,4-dimethylheptane, 3-ethyl-3-methylhexane, 4-ethylheptane, 2,3,3,4-tetramethylpentane, 2,3-dimethyl-3-ethylpentane, trans-1,2,3-trimethylcyclohexane, 1-isopropyl-e-methylcyclopentane (pulegan), 4-methyloctane, 1-isopropyl-2-methylcyclopentane, 3-ethylheptane, 2-methyloctane, cis-1,2,3-trimethylcyclohexane, 3-methyloctane, 2,4,6-trimethylheptane, cis-1,2,4-trimethylcyclohexane, 3,3-diethylpentane, 2,2-dimethyl-4-ethylhexane, 2,2,4-trimethylheptane, 2,2,4,5-tetramethylhexane, 2,2,5-trimethylheptane, 2,2,6-trimethylheptane, 2,2,3,5-tetramethylhexane, nopinane (7,7-dimethylbicyclo[3.1.1]heptane), trans-1-ethyl-r-methylcyclohexane, cycloctane, 1-ethyl-2-methylcyclohexane, n-nonane, 1,3,3-trimethylbicyclo[2.2.1]heptane (fenchane), trans-1-ethyl-4-methylcyclohexane, cis-1,1,3,5-tetramethylcyclohexane, cis-1-ethyl-4-methylcyclohexane, 2,5,5-trimethylheptane, 2,4,4-trimethylheptane, 2,3,3,5-tetramethylhexane, 2,2,4,4-tetramethylhexane, isopropylcyclohexane, 1,1,2,2-tetramethylcyclohexane, 2,2,3,4-tetramethylhexane, 2,2-dimethyloctane, 3-ethyl-2,2,4-trimethylpentane, 3,3,5-trimethylheptane, 2,3,5-trimethylheptane, 2,4-dimethyloctane, d,l-cis-1-ethyl-3-methylcyclohexane, d,l-2,5-dimethyloctane, 1,1,3,5-tetramethylcyclohexane, n-butylcyclopentane, n-propylcyclohexane, 2,3,5-trimethylheptane, 2,5-dimethyl-3-ethylhexane, 2,4,5-trimethylheptane, 2,4-dimethyl-3-isopropylpentane, 2,2,3-trimethylheptane, 2,4-dimethyl-4-ethylhexane, 2,2-dimethyl-3-ethylhexane, 2,2,3,4,4-pentamethylpentane, 1,1,3,4-tetramethylcyclohexane, 5-ethyl-2-methylheptane, 2,7-dimethyloctane, 3,6-dimethyloctane, 3,5-dimethyloctane, 4-isopropylheptane, 2,3,3-trimethylheptane, 4-ethyl-2-methylheptane, 2,6-dimethyloctane, 2,2,3,3-tetramethylhexane, trans-1-isopropyl-4-methylcyclohexane (p-menthane), 4,4-dimethyloctane, 2,3,4,5-tetramethylhexane, 5-ethyl-e-methylheptane, 3,3-dimethyloctne, 4,5-dimethyloctane, 3,4-diethylhexane, 4-propylheptane, 1,1,4-trimethylcycloheptane (eucarvane), trans-1,2,3,5-tetramethylcyclohexane, 2,3,4,4-tetramethylhexane, 2,3,4-trimethylheptane, 3-isopropyl-2-methylhexane, 2,2,7-trimethylbicyclo[2.2.1]heptane (a-frenchane), 3-methylheptane, 2,4-dimethyl-3-ethylhexane, 3,4,4-trimethylheptane, 3,3,4-trimethylheptane, 3,4,5-trimethylheptane, 2,3-dimemthyl-4-ethylhexane, 1-methyl-e-propylcyclohexane, 2,3-dimethyloctane, d,l-pinane, 2,3,3,4-tetramethylhexane, 3,3-dimethyl-4-ethylhexane, 5-methylnonane, 4-methylnonane, 3-ethyl-2-methylheptane, 3,4-dimethyloctane, d-a-pinane, d,l-1-isopropyl-3-methylcyclohexane (d,l-m-menthane), 2,2,3,3,4-pentamethylpentane, trans-1,2,4,5-tetramethylcyclohexane, 3,3-diethylhexane, 2-methylnonane, d-1-isopropyl-3-methylcyclohexane (d-m-menthane), 3-ethyl-4-methylheptane, 4-ethyl-3-methylheptane, 4-ethyl-4-methylheptane, 1-β-pinane, 3-methylnonane, 3-ethyloctane, 4-ethyloctane, 3-ethyl-2,2,3-trimethylpentane, 1-1-isopropyl-3-methylcyclohexane (1-m-menthane)cis-1-isopropyl-4-methylcyclohexane (cis-p-menthane), cis-1,2,3,5-tetramethylcyclohexane, 2,3-dimethyl-3-ethylhexane, 1-isopropyl-4-methylcyclohexane (p-menthane), 3,4-dimethyl-3-ethylhexane, 3,3,4,4-tetramethylhexane, cyclononane, 1-isopropyl-2-methylcyclohexane (o-menthane), cis-1,2,4,5-tetramethylcyclohexane, 1-methyl-1-propylcyclohexane, n-decane, 1-methyl-4-propylcyclohexane, 1-methyl-2-propylcyclohexane, n-pentrylcyclopentane, n-butylcyclohexane, trans-decahydronaphthalene (trans-decalin), isoamylcyclohexane, cis-decahydronaphthalene (cis-decalin), n-undecane (n-hendecane), cyclodecane, n-pentylcyclohexane, n-hexylcyclopentane, 9-methyl-trans-decahydronaphthalene, 1,10-dimethyl-trans-decahydronaphthalene, 9-methyl-cis-decahydronaphthalene, n-dodecane, 1,10-dimethyl-cis-decahydronaphthalene, n-hexycyclohexane, n-heptylcyclopentane, 9-ethyl-trans-decahydronaphthalene, 9-ethyl-cis-decahydronaphthalene, 1-methyl-trans-decahydronaphthalene, n-tridecane, bicyclohexyl, n-octylcyclopentane, n-heptylcyclohexane, n-tetradecane, n-nonylcyclopentane, n-octylcyclohexane, n-pentadecane, n-decylcyclopentane, n-nonylcyclohexane, n-undecylcyclopentane (n-hendecylcyclopentane), n-decylcyclohexane, 2-methylheptadecane, n-dodecylcyclopentane, n-undecylcyclohexane (n-hendecylcyclohexane), n-tridecylcyclopentane, n-dodecylcyclohexane, n-tetradecylcyclopentane, pentadecylcyclopentane, n-hexadecane (cetane), tridecylcyclohexane, hexadecicyclopentane, n-heptadecane, tetradecylcyclohexane, heptadecylcyclopentane, n-octadecane, pentadecylcyclohexane, octadecylcyclopentane, n-nonadecane, hexadecylcyclohexane, nonadecylcyclopentane, n-eicosane, heptadecylcyclohexane, eicosylcyclopentane, n-heneicosane, octadecylcyclohexane, heneicosylcyclopentane, n-docosane, docosylcyclopentane, nonadecylcyclohexane, n-tricosane, eicosylcyclohexane, tricosylcyclopentane, n-tetracosane, tetracosylcyclopentane, heneicosylcyclohexane, n-pentacosane, pentacosylcyclopentane, docosylcyclohexane, hexacosylcyclopentane, noticyclene (tricyclo[2.2.1.0²,⁶]heptane), n-hexacosane, cyclohexadecane, tricosylcyclohexane, heptacosylcyclopentane, n-heptacosane, tetracosylcyclohexane, cyclopentadecane, octacosylcyclopentane, n-octacosane, pentacosylcyclohexane, nonacosylcyclopentane, n-nonacosane, hexacosylcyclohexane, triacontylcyclopentane, d,l-isobornane(2,2,3-trimethylbicyclo[2.2.2]heptane), n-triacontane, heptacosylcyclohexane, hentriacontylcyclopentane, n-hentriacontane, octacosylcyclohexane, dotriacontylcyclopentane, n-dotriacontane (bicetyl), noncosylcyclohexane, tritriacontylcyclopentane, tritriacontane, triacontylcyclohexane, tetratriacontylcyclopentane, tetratriacontane, 28-methylnonacosane, hentriacontylcyclohexane, pentatriacontylcyclopentane, pentatriacontane, dotriacontylcyclohexane, hexatriacontylcyclopentane, hexatriacontane, tritriacontylcyclohexane, heptatriacontane, tetratriacontylcyclohexane, octatriacontane, pentatriacontylcyclohexane, nonatriacontane, hexatriacontylcyclohexane, tetracontane, norbornane (bicyclo[2.2.1]heptane], 2,2,3,3-tetramethylbutane, bornane (camphane), and adamantane. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid or phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Non-limiting examples of alkenyl groups include methylene, ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group may be optionally substituted with any moiety that does not adversely affect the reaction process, including but not limited to but not limited to hydroxyl, halo (F, Cl, Br, I), perfluoro alkyl including but not limited to trifluoromethyl, amino, alkylamino, arylamino, alkoxy, aryloxy, nitro, cyano, acyl, amido, carboxamido, carboxylate, thiol, alkylthio, azido, sulfonic acid, sulfate, phosphonic acid, phosphate, or phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl", alone or in combination, means a carbocyclic aromatic system containing one, two or three rings wherein such rings may be attached together in a pendent manner or may be fused. Non-limiting examples of aryl include phenyl, biphenyl, or naphthyl, or the following aromatic group that remains after the removal of a hydrogen from the aromatic ring: benzene, toluene, ethylbenzene, 1,4-xylene, 1,3-xylene, 1,2-xylene, isopropylbenzene (cumene), n-propylbenzene, 1-ethyl-3-methylbenzene (m-ethyltoluene), 1-ethyl-4-methylbenzene (p-ethyltoluene), 1,3,5-trimethylbenzene (mesitylene), 1-ethyl-2-methylbenzene (o-ethyltoluene), tert-butylbenzene, 1,2,4-trimethylbenzene (pseudodocumene), isobutylbenzene, sec-butylbenzene, 3-isopropyl-methylbenzene (3-isopropyltoluene; m-cymene), 1,2,3-trimethylbenzene (hemimellitene), trans-propenylbenzene, indane, 4-isopropyl-1-methylbenzene (4-isopropyltoluene; 4-cymene), 2-isopropyl-methylbenzene (2-isopropyltoluene; 2-cymene), 1,3-diethbenzene, 1 methyl-3-proplybenzene (m-propyltoluene), indene, n-butylbenzene, 1-methyl-4-propylbenzene (p-propyltoluene), 1,2-diethylbenzene, 1,4-diethylbenzene, 1,3-dimethyl-5-ethylbenzene, 1-methyl-2-propylbenzene (o-propyltoluene), 2,2-dimethyl-1-phenylpropane (neopentylbenzene), 1,4-dimethyl-2-ethylbenzene, 2-methylindane, 3-methyl-2-phenylbutane, 1-methylindane, 1,3-dimethyl-4-ethylbenzene, 3-tert-butyl-menthylbenzene, (3-tert-butyltoluene), 1,2-dimethyl-4-ethylbenzene, 1,3-dimethyl-2-ethylbenzene, 3-phenylpentane, 1-ethyl-3-isopropylbenzene, 2-methyl-2-phenylbutane, 4-tert-butyl1-methylbenzene (4-tert-butyltoluene), 1-ethyl-2-isopropylbenzene, 2-phenylpentane, 1,2-dimethyl-3-ethybenzene, 3-sec-butyl-1-methylbenzene, (3-sec-butylotoluene), 3-isobutyl-1-methylbenzene, (3-isobutyltoluene), d-2-methyl-1-phenylbutane, 1,3-dimethyl-5-isopropyl-benzene, 2-phenyl-cis-2-butene, 4-isobutyl-methylblenzene (p-isobutyltoluene), 2-sec-butyl-1-methylbenzene (2-sec-butyltoluene), 2-isobutyl-1-methylblenzene (o-isobutyltoluene), 1,4-dimethyl-2-isopropyl-benzene, 1-ethyl-4-isopropylbenzene, d,l-2-methyl-1-phenylbutane, 1,2,3,5-tetramethylbenzene (isodurene), 3-methyl-1-phenylbutane (isopentylbenzene), 1,3-dimethyl-2-isopropylbenzene, 1,3-dimethyl-4-isopropylbenzene), 3-methylindene, 4-sec-butyl-1-methylbenzene (p-sec-butyltoluene), 2-tert-butyl-1-methylbenzene (2-tert-butyltoluene), 3,5-diethyl-1-methylbenzene (3,5-diethyltoluene), 2-butyl-1-methylbenzene (2 butyltoluene), 1-ethyl-3-propylbenzene, 1,2-dimethyl-4-isopropylbenzene, 1,2-dimethyl-3-isopropylbenzene, 1-ethyl-2-propylbenzene, 1,3-di-isopropyllbenzene, 1,2-diethyl-4-methylbenzene, 1,2-di-isopropylbenzene, 1,4-dimethyl-2-proplybenzene, 1,2,3,4-tetramethylbenzene (prehnitene), 1-ethyl-4-propylbenzene, 3-butyl-1-methlybenzene (m-butyltoluene), 2,4-diethyl-1-methylbenzene (2,4-diethyltoluene), n-pentylbenzene, 3-methyl-3-phenylpentane, 1,3-dimethyl-5-tert-butylbenzene, 1,3-dimethyl-4-propylbenzene, 1,2-diethyl-3-methylbenzene, 4-butyl-1-methylbenzene, 4-butyl-1-methylbenzene, 1,2,3,4-tetrahydronaphthalene, 1,3-diethyl-2-propylbenzene, 2,6-diethyl-1-methylbenzene, 1,2-dimethyl-4-propylbenzene, 1,3-dimethyl-5-propylbenzene, 2-methyl-3-phenylpentane, 4-tert-butyl-1,3-dimethylbenzene, 1,4-di-isopropylbenzene, 1,2-dimethyl-3-propylbenzene, 1-teri-butyl-4-ethylbenzene, d,l-3-phenylhexane, 2-ethyly-1,3,5-trimethyl-benzene, 3-ethyly- 4-isopropyl-1-methylbenzene, 5-ethyl-1,2,4-trimethylbenzene, 6-ethyl-1-2,4-trimethylbenzene, 2-phenylhexane, 2-methyl-1-phenylpentane, 4-isopropyl-1-propylbenzene, 1,3-dipropylbenzene, 5-ethyl-1,2,3-trimethylbenzene, 1,2,4-triethylbenzene, 1,3,5-triethylbenzene, 2-methyl-1,2,3,4-tetrahydronaphthalene, 1-methyl-1,2,3,4-tetrahydronaphthalene, 4-ethyl-1,2,3-trimethylbenzene, 1,4-dipropylbenzene, 3-methyl-1-phenylpentane, 2-propyl-1,3,5-trimethylbenzene, 1,1-dimeihyl-1,2,3,4-tetrahydronaphthalene, 3-tert-butyl-1-isopropylbenzene, 1-methyl-3-pentylbenzene, 4-tert-butyl-1-isopropylbenzene, 2-methyl-2-phenylhexane, 2,4-di-isopropyl-1-methylbenzene, 3-methyl-3-phenylhexane, n-hexylbenzene, 3-phenylheptane, 2,6-di-isopropyl-1-methylbenzene, 5-propyl-1,2,4-trimethylbenzene, 6-methyl-1,2,3,4-tetrahydronaphthalene, 2,2-dimethyl-1,2,3,4-tetrahydronaphthalene, 2-phenylheptane, 5-methyl-1,2,3,4-tetrahydronaphthalene, 2-ethyl-1,2,3,4-tetrahydronaphthalene, cyclohexylbenzene, 1-ethyl-1,2,3,4-tetrahydronaphthalene, 2,5-dimethyl-1,2,3,4-tetrahydronaphthalene, 2,8-dimethyl-1,2,3,4-tetrahydronaphthalene, 2,7-dimethyl-1,2,3,4-tetrahydronaphthalene, 2,6-dimethyl-1,2,3,4-tetrahydronaphthalene, 1,4-di-sec-butylbenzene, 1,5-dimethyl-1,2,3,4-tetrahydronaphthalene, 3-ethyl-3-phenylhexane, 6-ethyl-1,2,3,4-tetrahydronaphthalene, 2-methyl-1-phenyl-1-butene, 5-ethyl-1,2,3,4-tetrahydronaphthalene, n-heptylbenzene, 1-methylnaphthalene, 5,6-dimethyl-1,2,3,4-tetrahydronaphthalene, 6,7-dimethyl-1,2,3,4-tetrahydronaphthalene, 5,7-dimethyl-1,2,3,4-tetrahydronaphthalene, 2-ethylnaphthalene, 1-7-dimethylnaphthalene, 1,6-dimethylnaphthalene, 1,3-dimethylnaphthalene, n-octylbenzene, 1-allylnaphthalene, 1-isopropylnaphthalene, 1,4-dimethylnaphthalene, 1,1-diphenylethane, 2-isopropylnaphthalene, 2-propylnaphthalene, 1-propylnaphthalene, 1,3,7-trimethylnaphthalene, 1-isopropyl-7-methylnaphthalene, n-nonylbenzene, 2-butylnaphthalene, 2-tert-butylnaphthalene, 1-tert-butylnaphthalene, 1-butylnaphthalene, 4,5-benzindane, n-decylbenzene, 1-pentylnaphthalene, 2-pentylnaphthalene, n-undecylbenzene, 1-hexylnaphthalene, 2-hexylnaphthalene, n-dodecylbenzene, 1-heptylnaphthalene, 2-heptylnaphthalene, tridecylbenzene, 1-octylnaphthalene, 2-octylnaphthalene, 1-nonylnaphthalene, 2-nonylnaphthalene, 1-decylnaphthalene, 1,2,6-trimethylnaphthalene, diphenylmethane, 1,2,3-trimethylnaphthalene, 1,6,7-trimethylnaphthalene, 2-isopropylazulene, 1,4-dimethyl-7-isopropylazulene, 2,6-dimethylphenanthrene, 1,2,5-trimethylnaphthalene, 1-propylphenanthrene, 5-isopropylazulene, 5-isopropylazulene, 2-propyl-phenanthrene, 2-methylnaphthalene, 1-ethyl-5-methylnaphthalene, 9-isopropylnaphthalene, 6-isopropylazulene, 2-ethyl-6-methylnaphthalene, 2-isopropylphenanthrene, 6-isopropyl-1-methylphenanthrene, 2-ethylazulene, 2,5,-dimethylphenanthrene, 1,3,5-trimethylnaphthalene, 3-ethyl-6-methylphenanthrene, 2-methylazulene, 1,3,8-trimethylnaphthalene; 4-methylphenanthrene, 1,4-dimethylphenanthrene, bibenzyl, methylenefluorene, 3,5-dimethylphenanthrene, 1,3-dimethylazulene, 7-methyl-3,4-benzphenanthrene, pentamethylbenzene, 1,2,4-trimethylnaphthalene, 3,3-dimethylstilbene, 1,4,5,7-tetramethylnaphthalene, 1,2,4,8-tetramethylnaphthalene, 2,9-dimethylphenanthrene, 1,5-dimethylphenanthrene, 2-benzylnaphthalene, 1-benzylnaphthalene, 1-benzylnaphthalene, 1,2-dimethylazulene, 9-propylphenanthrene, 1,7-dimethyl-4-isopropylnaphthalene, 3-methylphenanthrene, 3,4-dimethylphenanthrene, 1-ethylphenanthrene, sym-diphenylacetylene, 9-ethylphenanthrene, 1,4,5-trimethylnaphthalene, 4-methylfluorene, 1,4,6,7-tretramethylnaphthalene, 1,2,3-trimethylphenanthrene, 1,8-dimethylnaphthalene, 8-methyl-3,4-benzphenanthrene, 2-ethylphenanthrene, 3,4-benzphenanthrene, 1,3,7-trimethylphenanthrene, 4-isopropyl-1-methylphenanthrene, 4,8-dimethylazulene, biphenyl, 2-methyl-3,4-benzphenanthrene, 3-methylpyrene, 1,4,7-trimethylphenanthrene, 1,4-dimethylanthracene, 4,9-dimethyl-1,2-benzanthracene, benzalfluorene, 1,3-dimethylphenanthrene, 1-methyl-3,4-benzphenanthrene, 3-isopropyl-1-methylphenanthrene, 1,2-binaphthyl, 2,3-dimethylphenanthrene, 1-ethyl-2-methylphenanthrene, 1,5-dimethylnaphthalene, 6-methyl-3,4-benzphenanthrene, naphthalene, 1,3,6,8-tetramethylnaphthalene, 1-ethyl-7methylphenanthrene, 9-methylanthracene, 1-isopropyl-7-methylphenanthrene, 6-methylazulene, 1,3-dimethylanthracene, 2,2-dimethylstilbene, 1-methylanthracene, 1,7-dimethylphenanthrene, 1,6-diphenylnaphthalene, 1,6-dimethylphenanthrene, 1,9-dimethylphenanthrene, 9-methylphenanthrene, 1,2,10-trimethylanthracene, 7-ethyl-1-methylphenanthrene, triphenylmethane, 5-isopropylnaphthanthracene, 3,9-dimethyl-1,2-benzanthracene, 5,6-benzindane, 12-isopropylnaphthanthracene, acenaphthene, 2,7-dimethylnaphthalene, 7-isopropyl-1-methylfluorene, azulene, retene, phenanthrene, 2,7-dimethfylphenanthrene, 2,3,6-trimethfylnaphthalene, 2-phenylnaphthalene, 1,2,3,4-tetrahydroanthracene, 2,3-dimethylnaphthalene, ethylidenefluorene, 1,7-dimethylfuorene, 1,1-dinaphthylmethane, fluoranthrene, 2,6-dimethylnaphthalene, 2,4-dimethylphenanthrene, fluorene, 4,10-dimethyl-1,2-benzanthracene, 4h-cyclopenta(def) phenanthrene, 1,3,8-trimethylphenanthrene, 11-methylnaphthanthracene, 5-methylchrysene, 1,2,5,6-tetramethylnaphthalene, cyclohept(fg)acenaphthene, 1,2,7-trimethylphenanthrene, 1,10-dimethyl-1,2-dibenzanthracene, 9,10-dimethyl-1,2-benzanthracene, benz (bc)aceanthrylene, 1-methylphenanthrene, 1,6,7-trimethylphenanthrene, 1,1-diacenaphthene, trans-stilbene, 3,4-benzflurorene, 9-isopropylnaphthanthracene, 6-methylnaphthanthracene, 5,8-dimethyl-1,2-bezanthracene, 8-isopropylnaphthanthracene, 1,4,5,8-tetramethylnaphthalene, 12-methylnaphthanthracene, 2-methyl-1,2-benzpyrene, 1,5-dimethylanthracene, 7-methylnaphthanthracene, 3,6-dimethylphenanthrene, 5-methyl-3,4-benzphenanthrene, 1,4-dimethylchrysene, 1,2-dimethylphenanthrene, 8,10-dimethyl-1,2-benzanthracene, 1,2,8-trimethylphenanthrene, 3-methyl-1,2-benzpyrene, 9-methyl-1,2-benzpyrene, 9-phenylfluorene, 2-methylnaphthanthracene, pyrene, 9-methylnaphthanthracene, 4-methylchrysene, trans-trans-1,4-diphenyl-1,3-butadiene, cinnamalfluorene, 5-methylnaphthanthracene, 1,2-benzanthracene, 8-methylnaphthanthracene, 1,1-binaphthyl, di-1-naphthastibene, 6-methylchrysene, 3-methylnaphthanthracene, 2,6-dimethyl-1,2-benzanthracene, cyclopentadienophenanthrene, 10,11-benzfluoranthene, hexamethylbenzene, 3-methylchrysene, cholanthrene, 6-methyl-1,2-benzpyrene, 6,7-dimethyl-1,2-benzanthracene, 1,2-benzpyrene, 5,10-dimethyl-1,2-benzanthracene, 4,5-benzpyrene, 9,10-dimethylanthracene, 10-methylnaphthanthracene, 5,6-dimethyl-1,2-benzanthracene, 2,2-binaphthyl, 1,2-benfluorene, 1,8-dimethylphenanthrene, 8-methyl-1,2-benzpyrene, bifluorenylidene, 1,2,7,8-dibenzanthracene, 4-methylnaphthanthracene, 1,2,3,4-dibenzanthracene, di-2-fluorenylmethane, 2,3-benzfluorene, 5-methyl-1,2-benzpyrene, anthracene, 11,12-benzfluoranthene, 4-methyl-1,2-benzpyrene, 2,8-dimethylchrysene, 2-methylchrysene, 6,12-dimethylchrysene, 1,2-benzphenanthrene, di-2-naphthastilbene, 1-methylchrysene, 2,3,6,7-dibenzphenanthrene, 2,3,5,6-dibenzphenanthrene, 1,2,5,6-dibenzanthracene, perylene, picene, 1,2,3,4,5,6,7,8-tetrabenzanthracene, and coronene. The term aryl includes both substituted and unsubstituted moieties. The aryl group may be optionally substituted with any moiety that does not adversely affect the process, including but not limited to but not limited to halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene et al., *Protective Groups in Organic Synthesis*, John Wiley & Sons, Second Edition, 1991, hereby incorporated by reference. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy. The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic" refers to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen (F, Cl, Br, I), haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against Flaviviridae, or are metabolized to a compound that exhibits such activity.

Prodrugs also include natural or unnatural amino acid esters of the disclosed nucleosides (see, e.g., European Patent Specification No. 99493, the text of which is incorporated by reference, which describes amino acid esters of acyclovir, specifically the glycine and alanine esters which show improved water-solubility compared with acyclovir itself, and U.S. Pat. No. 4,957,924 (Beauchamp), which discloses the valine ester of acyclovir, characterized by side-chain branching adjacent to the a-carbon atom, which showed improved bioavailability after oral administration compared with the alanine and glycine esters). A process for preparing such amino acid esters is disclosed in U.S. Pat. No. 4,957,924 (Beauchamp), the text of which is incorporated by reference. As an alternative to the use of valine itself, a functional equivalent of the amino acid may be used (e.g., an acid halide such as the acid chloride, or an acid anhydride). In such a case, to avoid undesirable side-reactions, it may be is advantageous to use an amino-protected derivative.

IV. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including but not limited to, sulfate, nitrate, bicarbonate and carbonate salts.

Pharmaceutically acceptable salts may be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including but not limited to sugars, 1,2-diacylglycerol and alcohols. Many are described in R. Jones & N. Bischofberger, *Antiviral Research*, 27 (1995) 1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference: Kucera, L. S., N. Iyer, E. Leake, A. Raben, Modest E. K., D. L. W., and C. Piantadosi, "Novel membrane-interactive ether lipid analogs that inhibit infectious HIV-1 production and induce defective virus formation," *AIDS Res. Hum. Retroviruses*, 1990, 6, 491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest, "Synthesis and evaluation of novel ether lipid nucleoside conjugates for anti-HIV activity," *J. Med. Chem.*, 1991, 34, 1408–1414; Hosteller, K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3, -deoxythymidine," *Antimicrob. Agents Chemother.*, 1992, 36, 2025–2029; Hostetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.*, 1990, 265, 61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Yatvin et al.); U.S. Pat. No. 5,194,654 (Hostetler et al.), U.S. Pat. No. 5,223,263 (Hostetler et al.); U.S. Pat. No. 5,256,641 (Yatvin et al.); U.S. Pat. No. 5,411,947 (Hostetler et al.); U.S. Pat. No. 5,463,092 (Hostetler et al.); U.S. Pat. No. 5,543,389 (Yatvin et al.); U.S. Pat. No. 5,543,390 (Yatvin et al.); U.S. Pat. No. 5,543,391 (Yatvin et al.); and U.S. Pat. No. 5,554,728 (Basava et al.), all of which are incorporated by reference. Foreign patent applications that disclose lipophilic substituents that can be attached to nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

V. Combination or Alternation Therapy

In another embodiment for the treatment of HIV or HBV infection, the active compound or its prodrug or salt can be administered in combination or alternation with another antiviral agent, such as another active anti-HIV or anti-HBV agent, including but not limited to those of the formulae above, others listed below or known in the art. In general, in combination therapy, effective dosages of two or more agents are administered together, whereas during alternation therapy, an effective dosage of each agent is administered serially. The dosage will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

Hepatitis B Therapies

| Drug Name | Drug Class | Company |
|---|---|---|
| Intron A (interferon alfa-2b) | interferon | Schering-Plough |
| Epivir-HBV (lamivudine; 3TC) | nucleoside analogue | GlaxoSmithKline |
| Hepsera (Adefovir Dipivoxi)" | nucleotide analogue | Gilead Sciences |
| Coviracil (emtricitabine; FTC) | nucleoside analogue | Triangle Pharmaceuticals |
| Entecavir | nucleoside analogue | Bristol-Myers Squibb |
| Clevudine (L-FMAU) | nucleoside analogue | Triangle Pharmaceuticals |
| ACH 126, 443 (L-Fd4C) | nucleoside analogue | Achillion Pharmaceuticals |
| AM 365 | nucleoside analogue | Amrad |
| Amdoxovir (formerly DAPD) | nucleoside analogue | Triangle Pharmaceuticals |
| LdT (telbivudine) | nucleoside analogue | Idenix |
| XTL 001 | monoclonal antibody | XTL Biopharm |
| Theradigm | Immune stimulant | Epimmune |
| Zadaxin (thymosin) | Immune stimulant | SciClone |
| EHT 899 | viral protein | Enzo Biochem |
| HBV DNA vaccine | Immune stimulant | PowderJect (UK) |
| MCC 478 | nucleoside analogue | Eli Lilly |
| valLdC (valtorcitabine) | nucleoside analogue | Idenix |
| ICN 2001 | nucleoside analogue | ICN |
| Fluro L and D nucleosides | nucleoside analogue | Pharmasset |
| Racivir | nucleoside analogue | Pharmasset |
| Robustaflavone | nucleoside analogue | Advanced Life Sciences |
| Penciclovir | | |
| DXG | | |
| HDP-P-acyclovir | | |
| LM-019c | | |
| CS-109 | | |
| PS-019 | | |
| PS-018 | | |
| ara-AMP prodrugs | | |
| HBV/MF59 | | |
| Hammerhead ribozymes | | |
| Glycosidase Inhibitors | | |
| Pegylated Interferon | | |
| Human Monoclonal Antibodies | | |
| Famciclovir | | |

HIV Therapies: Protease Inhibitors (PIs)

| Brand Name | Generic Name | Abbreviation | Pharmaceutical Company |
|---|---|---|---|
| Invirase ® | saquinavir (Hard Gel Cap) | SQV (HGC) | Hoffmann-La Roche |
| Fortovase ® | saquinavir (Soft Gel Cap) | SQV (SGC) | Hoffmann-La Roche |
| Norvir ® | ritonavir | RTV | Abbott Laboratories |
| Crixivan ® | indinavir | IDV | Merck & Co. |
| Viracept ® | nelfinavir | NFV | Pfizer |
| Agenerase ® | amprenavir | APV | GlaxoSmithKline |
| Kaletra ® | lopinavir + ritonavir | LPV | Abbott Laboratories |
| | fosamprenavir | | GlaxoSmithKline |
| | tipranavir | TBV | Boehringer Ingelheim |
| | atazanavir | | Bristol-Myers Squibb |

HIV Therapies: Nucleoside/Nucleotide Reverse Transcriptase Inhibitors (NRTIs)

| Brand Name | Generic Name | Abbreviation | Pharmaceutical Company |
|---|---|---|---|
| Retrovir ® | zidovudine | AZT or ZDV | GlaxoSmithKline |
| Epivir ® | lamivudine | 3TC | GlaxoSmithKline |
| Combivir ® | zidovudine + lamivudine | AZT + 3TC | GlaxoSmithKline |
| Trizivir ® | abacavir + zidovudine + lamivudine | ABC + AZT + 3TC | GlaxoSmithKline |
| Ziagen ® | abacavir | ABC | GlaxoSmithKline |
| Hivid ® | zalcitabine | ddC | Hoffmann-La Roche |
| Videx ® | didanosine: buffered versions | ddI | Bristol-Myers Squibb |
| Videx ® EC | didanosine: delayed-release capsules | ddI | Bristol-Myers Squibb |
| Zerit ® | stavudine | d4T | Bristol-Myers Squibb |
| Viread ™ | tenofovir disoproxil fumarate (DF) | TDF or Bis(POC) PMPA | Gilead Sciences |
| Coviracil ™ | emtricitabine | FTC | Triangle Pharmaceuticals |
| | amdoxovir | DAPD | Triangle Pharmaceuticals |

HIV Therapies: Non-Nucleoside Reverse Transcriptase Inhibitors (NNRTIs)

| Brand Name | Generic Name | Abbreviation | Pharmaceutical Company |
|---|---|---|---|
| Viramune ® | nevirapine | NVP | Boehringer Ingelheim |
| Rescriptor ® | delavirdine | DLV | Pfizer |
| Sustiva ® | efavirenz | EFV | Bristol-Myers Squibb |
| | (+)-calanolide A | | Sarawak Medichem Pfizer Bristol-Myers Squibb Tibotec-Virco Group |
| | capravirine | CPV | Tibotec-Virco Group |

| Brand Name | Generic Name | Abbreviation | Pharmaceutical Company |
|---|---|---|---|
| HIV Therapies: Other Classes of Drugs | | | |
| Viread ™ | tenofovir disoproxil fumarate (DF) | TDF or Bis(POC) PMPA | Gilead Sciences |
| Cellular Inhibitors | | | |
| Droxia ® | hydroxyurea | HU | Bristol-Myers Squibb |
| Entry Inhibitors (including Fusion Inhibitors) | | | |
| Fuzeon ™ | enfuvirtide | | Trimeris Trimeris AnorMED, Inc. Progenics Pharmaceuticals |

| Brand Name | Generic Name | Abbreviation | Pharmaceutical Company |
|---|---|---|---|
| HIV Therapies: Immune-Based Therapies | | | |
| Proleukin ® | aldesleukin, or Interleukin-2 | IL-2 | Chiron Corporation |
| Remune ® | HIV-1 Immunogen, or Salk vaccine | | The Immune Response Corporation HollisEden Pharmaceuticals |

| Brand Name | Generic Name | Side Effect | Pharmaceutical Company |
|---|---|---|---|
| HIV Therapies: Treatments for Side Effects | | | |
| Procrit ® | epoetin alfa (erythropoietin) | Anemia | Ortho Biotech |
| Serostim ® | somatropin, or human growth hormone | Lipodystrophy | Serono Laboratories |

In one embodiment, the compounds of the invention may be employed together with at least one other antiviral agent chosen from reverse transcriptase inhibitors, protease inhibitors, fusion inhibitors, entry inhibitors and polymerase inhibitors.

In addition, compounds according to the present invention can be administered in combination or alternation with one or more anti-retrovirus, anti-HBV, anti-HCV or anti-herpetic agent or interferon, anti-cancer or antibacterial agents, including but not limited to other compounds of the present invention. Certain compounds according to the present invention may be effective for enhancing the biological activity of certain agents according to the present invention by reducing the metabolism, catabolism or inactivation of other compounds and as such, are co-administered for this intended effect.

VI. Pharmaceutical Compositions

Host, including but not limited to humans, infected with a human immunodeficiency virus, a hepatitis virus, or a gene fragment thereof, can be treated by administering to the patient an effective amount of the active compound or a pharmaceutically acceptable prodrug or salt thereof in the presence of a pharmaceutically acceptable carrier or diluent.

The active materials can be administered by any appropriate route, for example, orally, parenterally, intravenously, intradermally, subcutaneously, or topically, in liquid or solid form.

A preferred dose of the compound for an HIV or HBV infection will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 3000 mg, preferably 70 to 1400 mg of active ingredient per unit dosage form. An oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (incorporated by reference). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VII. Processes for the Preparation of Active Compound

A process for the facile preparation of $N^4$-acyl-cytosine-1,3-dioxolane nucleosides is also provided. The method includes condensation of a 5'-O-silyl protected 5-fluorocytidine-1,3-dioxolane, with either a carboxylic acid chloride, or carboxylic acid anhydride, or a carboxylic acid, followed by desilylation. The other $N^4$-acyl-substituted cytosine nucleosides can be synthesized using the similar approaches.

The $N^4$-acyl-substituted 5-fluorocytidine-1,3-dioxolane disclosed herein can be prepared as described in detail below, or by other assays known to those skilled in the art.

The present invention is further illustrated in the following examples. It will be understood by one of ordinary skill in the art that these examples are in no way limiting and that variations of detail can be made without departing from the spirit and scope of the present invention.

EXAMPLES

Anhydrous solvents were purchased from Aldrich Chemical Company, Inc. (Milwaukee). Melting points (mp) were determined on an Electrothermal digit melting point apparatus and are uncorrected. $^1H$ and $^{13}C$ NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were recorded on a JEOL JMS-SX/SX102A/E mass spectrometer. Elemental analyses were performed by Atlantic Microlab Inc. (Norcross, GA). Analytic TLC was performed on Whatman LK6F silica gel plates, and preparative TLC on Whatman PK5F silica gel plates. Column chromatography was carried out on Silica Gel (Fisher, S733-1) at atmospheric pressure.

Example 1

General Process for the Preparation of 1,3-DioxolaneIntermediate(i)

The 1,3-dioxolane intermediate (i) of the present invention can be synthesized according to U.S. Pat. No. 5,041,449, filed Jun. 29, 1990; U.S. Pat. No. 5,270,315, filed Mar. 7, 1991 ("2-Substituted-4-substituted-1,3-dioxolanes, synthesis and use thereof"); PCT application CA 92/00209, filed May 20, 1992; U.S. Pat. No. 5,756,706, filed May 13, 1994; U.S. Pat. No. 5,744,596, filed Jun. 5, 1995 ("Processes for diastereoselective synthesis of nucleosides"); PCT Application CA 94/00311, filed Jun. 7, 1994; U.S. Pat. No. 5,763,606, filed Feb. 2, 1995 ("Stereoselective synthesis of nucleoside analogues using bicyclic intermediate"); U.S. Patent Application 60/119,756, filed Feb. 11, 1999; U.S. Patent Application 60/119,885, filed Feb. 12, 1999; PCT Application CA 00/00144, filed Feb. 11, 2000; U.S. patent application Ser. No. 09/890,283, filed Feb. 11, 2000 (Stereoselective Synthesis Of Nucleoside Analogues); U.S. Patent Application 60/181,977, filed Feb. 11, 2000; U.S. patent application Ser. No. 09/779,853, filed Feb. 9, 2001; PCT Application CA 01/00117, filed Feb. 2, 2001 (Stereoselective Synthesis Of Nucleoside Analogues); U.S. Patent Application 60/350968, filed Jan. 25, 2002 (Process for producing dioxolane nucleoside analogues) or any manner known to those of ordinary skills in the art.

Additionally, the 1,3-dioxolane intermediate can also be prepared according to the process as set forth in U.S. Pat. No. 5,444,063, filed Oct. 28, 1992; U.S. Pat. No. 5,684,010, filed Jun. 6, 1995; U.S. Pat. No. 5,834,474, filed Apr. 15, 1997; U.S. Pat. No. 5,830,898, filed Apr. 15, 1997; PCT Application WO 94/09793, filed Oct. 28, 1993 ("Enantiomerically β-D-Dioxolane Nucleosides with Selective Anti-Hepatitis B Virus Activity"); U.S. Pat. No. 5,179,104, filed Dec. 5, 1990; PCT Application WO 92/10497, filed Dec. 5, 1990 ("Process for the preparation of enantiomerically pure β-D-(−)-dioxolane"); U.S. Pat. No. 5,767,122, filed Jun. 6, 1995 ("Enantiomerically pure β-D-(−)-dioxolane-nucleosides"); U.S. Pat. No. 5,276,151, filed Dec. 6, 1991 ("Method of Synthesis of 1,3-Dioxolane Nucleosides"); U.S. patent application Ser. No. 09/669,806, filed Sep. 26, 2000 ("Method of Manufacture of 1,3-Oxathiolane Nucleosides"); U.S. Patent Application No. 60/106,664, filed Nov. 2, 1998; U.S. patent application Ser. No. 09/432,247, filed Nov. 2, 1999; and PCT Application WO 00/25797, filed Nov. 2, 1999 ("Combination Therapy to Treat Hepatitis B Virus"); U.S. patent application Ser. No. 10/023,636, filed Dec. 17, 2001; PCT Application US 01/48817, filed Dec. 17, 2001 ("DAPD Combination Therapy with Ribavirin or Mycophenolic Acid"); and U.S. Patent Application No. 60/393,935, filed Jul. 3, 2002 ("Combination Therapy with 1,3, -Dioxolanes and Inosine Monophosphate Dehydrogenase Inhibitors"), all assigned to Emory University, Atlanta, Ga., USA.

Example 2

General Process for Acylation of 1,3-Dioxolane

The 1,3-dioxolane intermediate (i) is protected at the 5'-hydroxyl with any known method known in the art. The protected 1,3-dioxolane (ii) is then acylated and deprotected to form the $N^4$-acylcytosine-1,3-dixolane nucleoside of formula (iv). See Scheme 1.

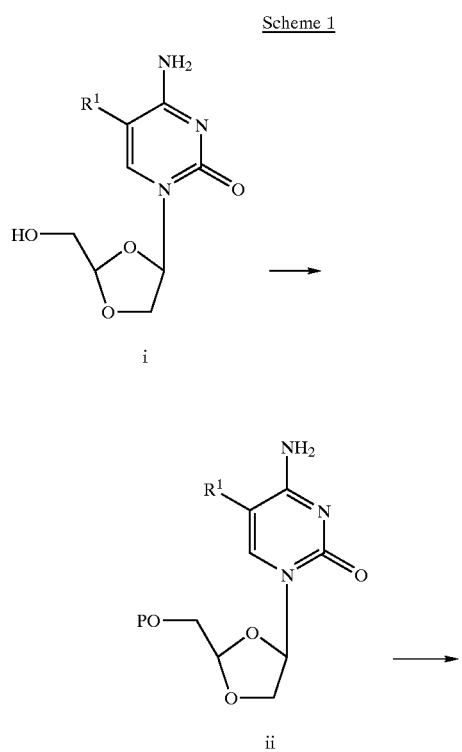

Scheme 1

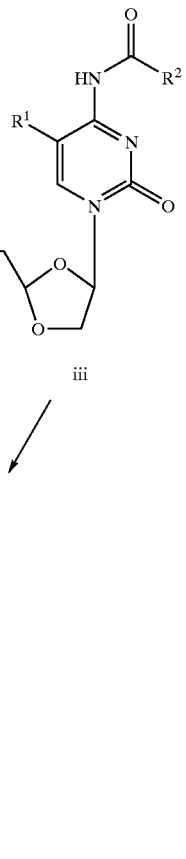

Wherein are $R^1$ is hydrogen or F; P is an oxygen protecting group; and $R^2$ is chosen from alkyl, alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen (F, Cl, Br, I), CN, $CF_3$, $N_3$, $NO_2$, alkyl, haloalkyl, aminoalkyl, alkoxy, thioalkyl, alkenyl, alkynyl, and aryl.

Example 3

β-D-5-fluoro-$N^4$-(4-iodobenzoyl)cytidine-1',3'-dioxolane (vi)

To a solution of (ii) and DMAP in anhydrous $CH_2Cl_2$ and $Et_3N$ at 0° C. was added 4-iodobenzoyl chloride. The reaction mixture was stirred at 0° C. for 30 min, then at room temperature for another 3 h. After removal of the solvent by evaporation, the residue was mixed with THF, and TBAF was added. After stirring for 2 h at room temperature, the solvent was evaporated, and the residue was purified by flash chromatography on silica gel eluting with $CH_2Cl_2$/MeOH (96:4) to give, after recrystallization from $CH_2Cl_2$/hexane, the title compound vi as a yellow powder.

Example 4

βD-$N^4$-Butyryl-5-fluorocytidine-1,3-dixolane (vii)

To a solution of ii and DMAP in anhydrous $CH_2Cl_2$ and $Et_3N$ at 0° C. was added butyric anhydride. The reaction mixture was stirred at 0° C. for 30 min, then at room temperature for another 2 h. After removal of the solvent by evaporation, the residue was mixed with THF, and TBAF was added. After stirring for 2 h at room temperature, the solvent was evaporated, and the residue was purified by flash chromatography on silica gel eluting with $CH_2Cl_2$/MeOH (96:4) to give, after recrystallization from $CH_2Cl_2$/hexane, the title compound vii.

Example 5

β-D-5-fluoro-$N^4$-(4-fluorobenzoyl)cytidine-1,3-dioxolane (viii)

To a solution of ii and DMAP in anhydrous $CH_2Cl_2$ and $Et_3N$ at 0° C. was added 4-fluorobenzoyl chloride. The reaction mixture was stirred at 0° C. for 30 min, then at room temperature for another 2 h. After removal of the solvent by evaporation, the residue was mixed with THF, and TBAF was added. After stirring for 2 h at room temperature, the solvent was evaporated, and the residue was purified by flash chromatography on silica gel eluting with $CH_2Cl_2$/MeOH (96:4) to give, after recrystallization from $CH_2Cl_2$/hexane, the title compound.

Example 6

Anti-HIV (in PBM Cells) Assay

Anti-HIV-1 activity of the compounds was determined in human peripheral blood mononuclear (PBM) cells as described previously (Schinazi R. F., McMillan A., Cannon D., Mathis R., Lloyd R. M. Jr., Peck A., Sommadossi J.-P., St. Clair M., Wilson J., Furman P. A., Painter G., Choi W.-B., Liotta D.C. Antimicrob. Agents Chemother. 1992, 36, 2423; Schinazi R. F., Sommadossi J.-P., Saalmann V., Cannon D., Xie M.-Y., Hart G., Smith G., Hahn E. Antimicrob. Agents Chemother. 1990, 34, 1061). Stock solutions (20–40 mM) of the compounds were prepared in sterile DMSO and then diluted to the desired concentration in growth medium. Cells were infected with the prototype HIV-$1_{LAI}$ at a multiplicity of infection of 0.01. Virus obtained from the cell supernatant was quantified on day 6 after infection by a reverse transcriptase assay using $(rA)_n \cdot (dT)_{12-18}$ as template-primer. The DMSO present in the diluted solution (<0.1%) had no effect on the virus yield. AZT was included as positive control. The antiviral $EC_{50}$ and $EC_{90}$ were obtained from the concentration-response curve using the median effective method described previously (Chou T.-C. & Talalay P. Adv. Enzyme Regul. 1984, 22, 27–55; Belen'kii M. S. & Schinazi R. F. Antiviral Res. 1994, 25, 1–11).

Example 7

Anti-HIV (in MT-2 Cells) Assay

In a second antiviral testing system, the potency of the compounds was determined by measurement of viral RNA accumulation in HIV-$1_{RF}$ infected MT-2 cells (Bacheler L T, Paul M, Otto M J, Jadhav P K, Stone B A & Miller J A (1994) An assay for HIV RNIn infected cell lysates, and its use for rapid evaluation of antiviral efficacy. Antivir. Chem. Chemother. 5:111–121). The virus titer was established to determine the dilution producing 15 to 30 ng/RNA per well of HIV RNIn 3 days of infection. HIV-1 RNA was quantified using biotinylated capture and alkaline phosphatase-derivatized reporter oligonucleotides as described previously (Charvet A-S, Camplo M, Faury P, Graciet J C, Mourier N, Chermann J C & Kraus J L (1994) Inhibition of human immunodeficiency virus type 1 replication by phosphonoformate- and phosphonoacetate-2',3'-dideoxy-3'-thiacytidine conjugates. J. Med. Chem. 37:2216–2223). In a third system, the effect of analogs on the replication of HIV-$I_{NL4-3}$ was determined via the InterCompany Consortium consensus p24 assay as previously described (Jadhav P K & MacKay M F (1997) Cyclic urea amide: HIV-1 protease inhibitors with low nanomolar potency against both wild types and protease inhibitor resistant mutants of HIV. J. Med. Chem. 40:181–190). Recombinant viruses were recovered by transfecting the appropriate NL4-3 plasmid by lipofection. Virus stocks recovered 7 to 10 days post-transfection were titered on MT-4 cells to determine if the dilution produced 1,000 to 3,000 ng p24 in 4 days. This dilution was then used in drug susceptibility assays, where drug was added 24 h post infection of cells, and $p2^4$ quantified by ELISA 3 days later.

Example 8

Anti-HBV Assay

The anti-HBV activity of the compounds was determined by treating the AD-38 cell line carrying wild type HBV under the control of tetracycline (Ladner S. K., Otto M. J., Barker C. S., Zaifert K., Wang G. H., Guo J. T., Seeger C. & King R. W. Antimicrob. Agents Chemother. 1997, 41, 1715–1720). Removal of tetracycline from the medium [Tet(−)] results in the production of HBV. The levels of HBV in the culture supernatant fluids from cells treated with the compounds were compared with that of the untreated controls. Control cultures with tetracycline [Tet(+)] were also maintained to determine the basal levels of HBV expression. 3TC was included as positive control.

Example 9

Cytotoxicity Assay

The toxicity of the compounds was assessed in Vero, human PBM, CEM (human lymphoblastoid), MT-2, and HepG2 cells, as described previously (Schinazi R. F., Sommadossi J.-P., Saalmann V., Cannon D. L., Xie M.-Y., Hart G. C., Smith G. A. & Hahn E. F. Antimicrob Agents Chemother. 1990, 34, 1061–1067). Cycloheximide was included as positive cytotoxic control, and untreated cells exposed to solvent were included as negative controls. The cytotoxicity $IC_{50}$ was obtained from the concentration-response curve using the median effective method described previously (Chou T.-C. & Talalay P. Adv. Enzyme Regul. 1984, 22, 27–55; Belen'kii M. S. & Schinazi R. F. Antiviral Res. 1994, 25, 1–11).

We claim:
1. A compound of the formula:

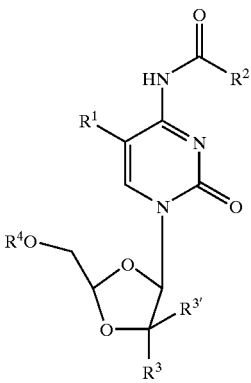

or a pharmaceutically acceptable salt thereof, wherein
i) $R^1$ is chosen from hydrogen and halogen;
ii) $R^2$ is chosen from alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen, CN, $CF_3$, $N_3$, $NO_2$, alkyl, haloalkyl, aminoalkyl, alkoxy, thioalkyl, alkenyl, alkynyl, and aryl;
iii) $R^3$ is chosen from halogen, CN, $CF_3$, $N_3$, $NO_2$, alkyl, alkenyl, and alkynyl;
iv) $R^{3'}$ is chosen from H, halogen methyl or ethyl; and
v) $R^4$ is H, phosphate, carbonyl substituted with alkyl, alkenyl, alkynyl, aryl, sulfonate ester, a lipid, an amino acid, a peptide, or cholesterol.

2. The compound of claim 1 wherein $R^1$ is fluorine.
3. The compound of claim 1 wherein $R^3$ is fluorine and $R^{3'}$ is H.
4. A compound selected from the group consisting of β-D-$N^4$-p-iodobenzoyl-5-fluorocytidine-1,3-dioxolane, β-D-$N^4$-p-fluoro-benzoyl-5-fluorocytidine-1,3-dioxolane, β-D-$N^4$-p-chlorobenzoyl-5-fluoro-cytidine-1,3-dioxolane, β-D-$N^4$-p-bromobenzoyl-5-fluorocytidine-1,3-dioxolane, β-D-$N^4$-p-ethyl-benzoyl-5-fluorocytidine-1,3-dioxolane, β-D-$N^4$-p-t-butylbenzoyl-5-fluoro-cytidine-1,3-dioxolane.

5. A compound selected from the following, or its pharmaceutically acceptable salt:

β-D-5-fluoro-$N^4$-(4-iodobenzoyl)cytidine-1,3-dioxolane of the structure:

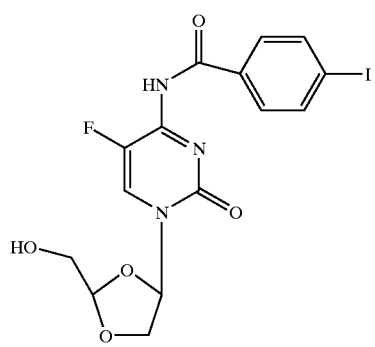

β-D-5-fluoro-$N^4$-(4-fluorobenzoyl)cytidine-1,3-dioxolane of the structure:

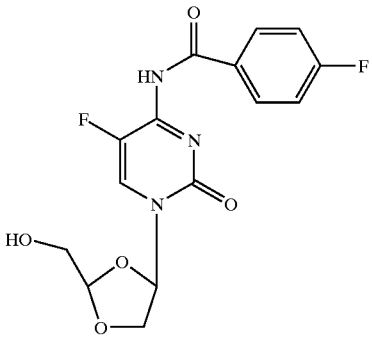

β-D-$N^4$-(4-chlorobenzoyl)-5-fluorocytidine-1,3-dioxolane of the structure:

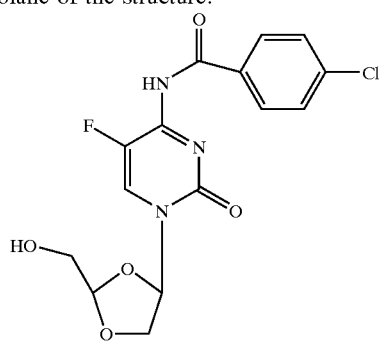

β-D-$N^4$-(4-bromobenzoyl)-5-fluorocytidine-1,3-dioxolane of the structure:

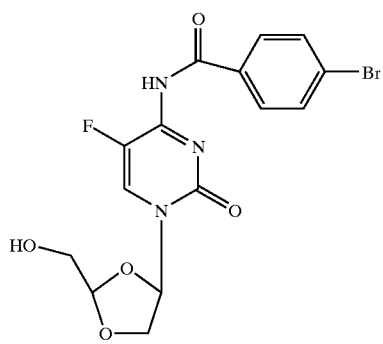

β-D-5-fluoro-$N^4$-(3-fluorobenzoyl)cytidine-1,3-dioxolane of the structure:

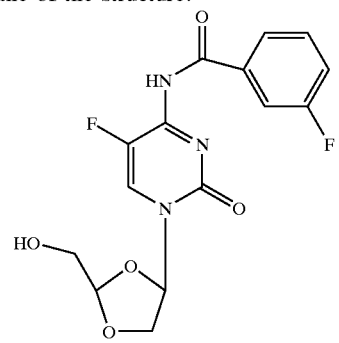

β-D-N⁴-(3-chlorobenzoyl)-5-fluorocytidine-1,3-dioxolane of the structure:

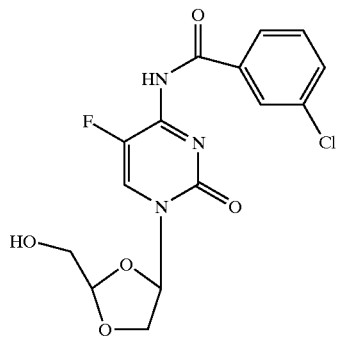

β-D-5-fluoro-N⁴-p-toluoylcytidine-1,3-dioxolane of the structure:

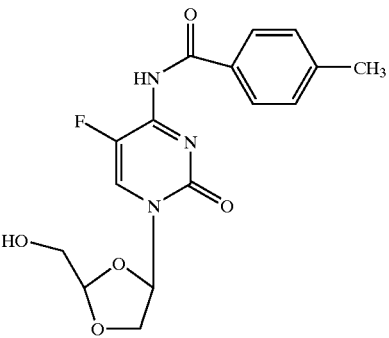

β-D-N⁴-(3-bromobenzoyl)-5-fluorocytidine-1,3-dioxolane of the structure:

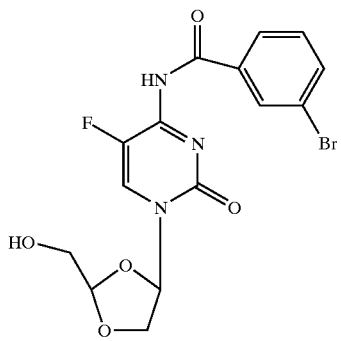

β-D-5-fluoro-N⁴-(m-toluoyl)cytidine-1,3-dioxolane of the structure:

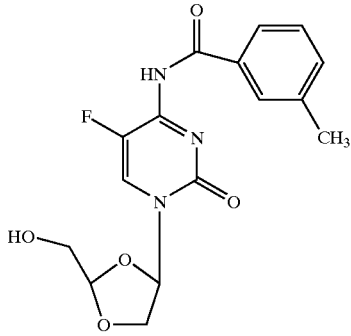

β-D-5-fluoro-N⁴-(4-nitrobenzoyl)cytidine-1,3-dioxolane of the structure:

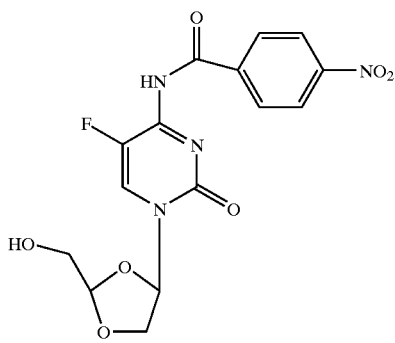

β-D-N⁴-(4-ethylbenzoyl)-5-fluorocytidine-1,3-dioxolane of the structure:

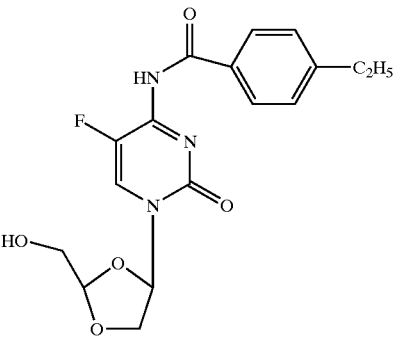

β-D-5-fluoro-N⁴-(4-propylbenzoyl)cytidine-1,3-dioxolane of the structure:

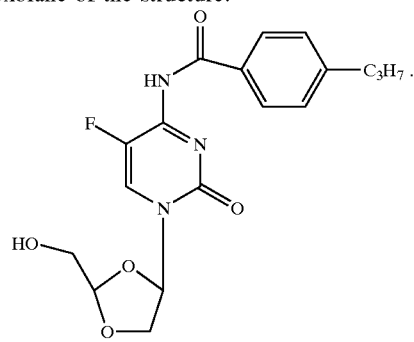

β-D-N⁴-(4-tert-butylbenzoyl)-5-fluorocytidine-1,3-dioxolane of the structure:

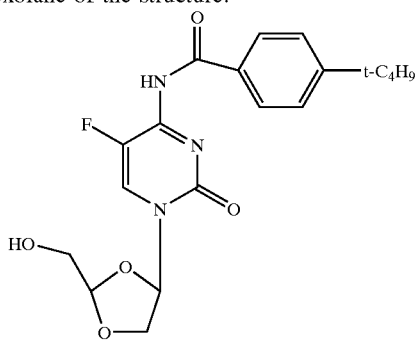

β-D-5-fluoro-N⁴-(2-thiophenecarbonyl)cytidine-1,3-dioxolane of the structure:

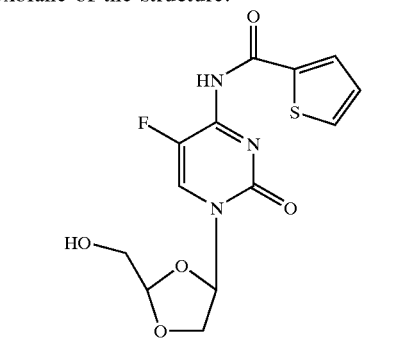

β-D-N⁴-(benzo-[b]-thiophene-2-carbonyl)-5-fluorocytidine-1,3-dioxolane of the structure:

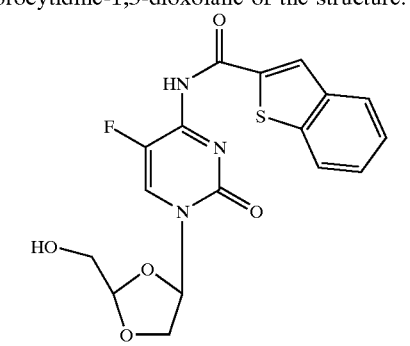

and β-D-N⁴-(cyclohexane-carbonyl)-5-fluorocytidine-1,3-dioxolane of the structure:

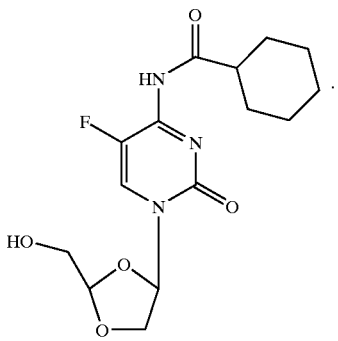

6. The compound of claim 5 wherein the compound is:
β-D-5-fluoro-N⁴-(iodobenzoyl)cytidine-1,3-dioxolane of the structure:

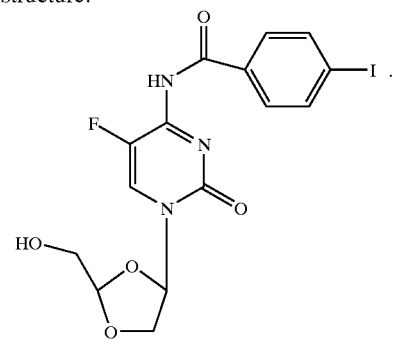

7. The compound of claim 5 wherein the compound is:
β-D-5-fluoro-N⁴-(4-fluorobenzoyl)cytidine-1,3-dioxolane of the structure:

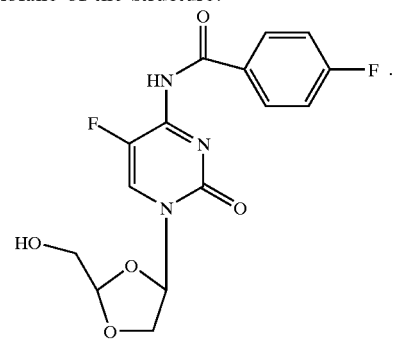

8. The compound of claim 5 wherein the compound is:
β-D-N⁴-(4-chlorobenzoyl)-5-fluorocytidine-1,3-dioxolane of the structure:

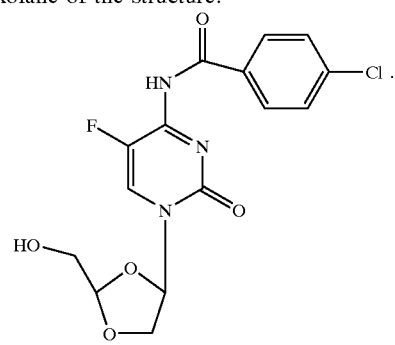

9. The compound of claim 5 wherein the compound is:
β-D-N⁴-(4-bromobenzoyl)-5-fluorocytidine-1,3-dioxolane of the structure:

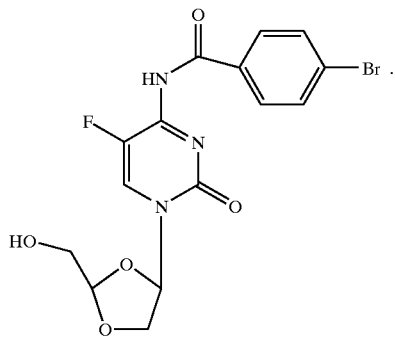

10. The compound of claim 5 wherein the compound is:
β-D-5-fluoro-N⁴-(3-fluorobenzoyl)cytidine-1,3-dioxolane of the structure:

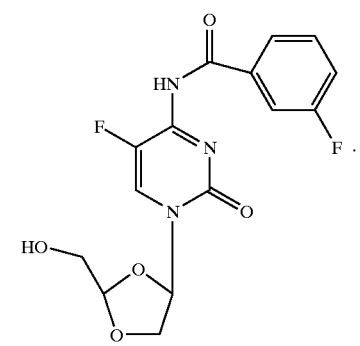

11. The compound of claim 5 wherein the compound is:
β-D-N⁴-(3-chlorobenzoyl)-5-fluorocytidine-1,3-dioxolane of the structure:

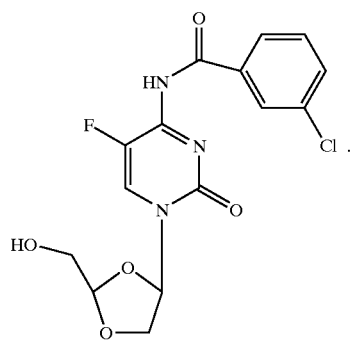

12. The compound of claim 5 wherein the compound is:
β-D-N⁴-(3-bromobenzoyl)-5-fluorocytidine-1,3-dioxolane of the structure:

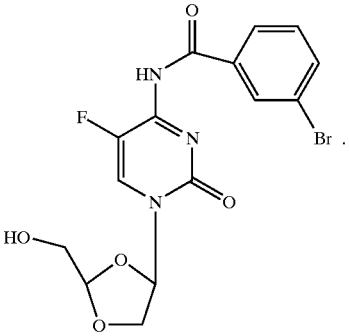

13. The compound of claim 5 wherein the compound is:
β-D-5-fluoro-N⁴-(4-nitrobenzoyl)cytidine-1,3-dioxolane of the structure:

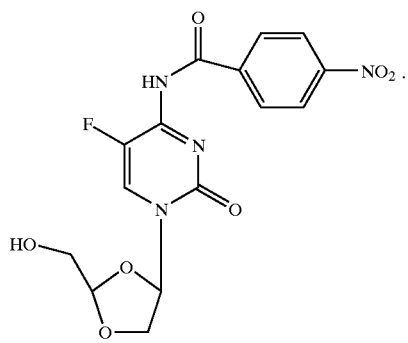

14. The compound of claim 5 wherein the compound is:
β-D-5-fluoro-N⁴-p-toluoylcytidine-1,3-dioxolane of the structure:

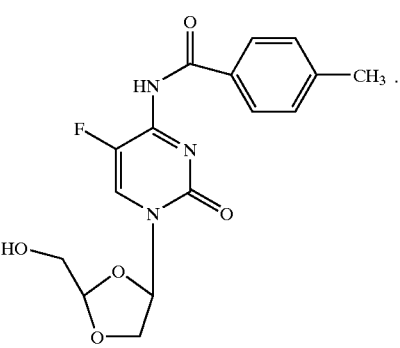

15. The compound of claim 5 wherein the compound is:
β-D-5-fluoro-N⁴-(m-toluoyl)cytidine-1,3-dioxolane of the structure:

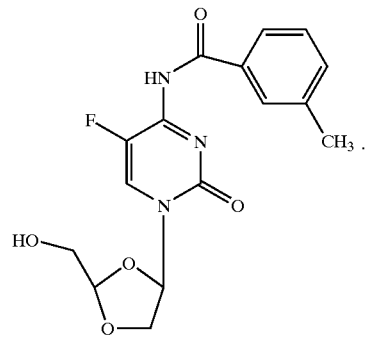

16. The compound of claim 5 wherein the compound is:

β-D-N$^4$-(4-ethylbenzoyl)-5-fluorocytidine-1,3-dioxolane of the structure:

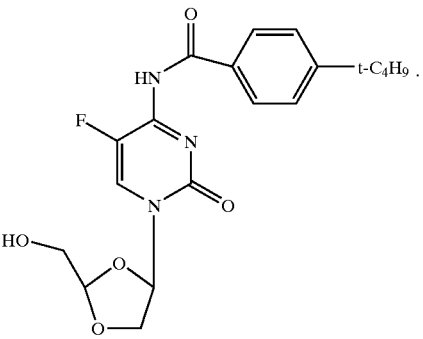

19. The compound of claim 5 wherein the compound is:

β-D-N$^4$-(cyclohexane-carbonyl)-5-fluorocytidine-1,3-dioxolane of the structure:

17. The compound of claim 5 wherein the compound is:

β-D-5-fluoro-N$^4$-(4-propylbenzoyl)cytidine-1,3-dioxolane of the structure:

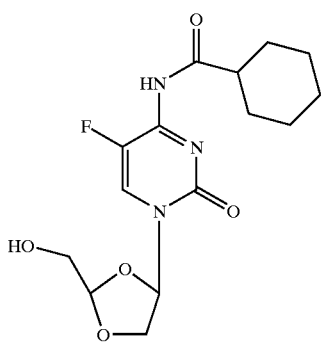

20. The compound of claim 5 wherein the compound is:

β-D-5-fluoro-N$^4$-(2-thiophenecarbonyl)cytidine-1,3-dioxolane of the structure:

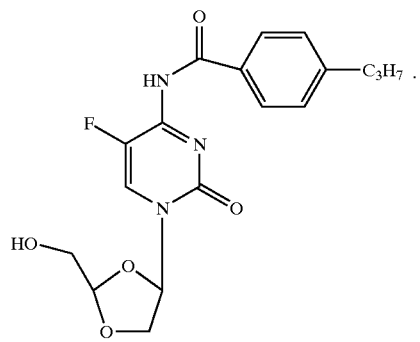

18. The compound of claim 5 wherein the compound is:

β-D-N$^4$-(4-tert-butylbenzoyl)-5-fluorocytidine-1,3-dioxolane of the structure:

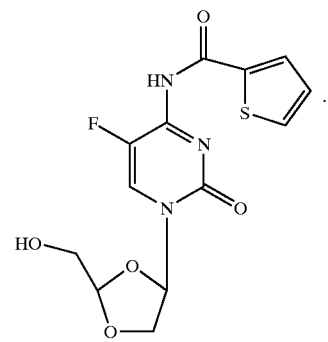

21. The compound of claim 5 wherein the compound is;

β-D-N$^4$-(benzo-[b]-thiophene-2-carbonyl)-5-fluorocytidine-1,3-dioxolane of the structure:

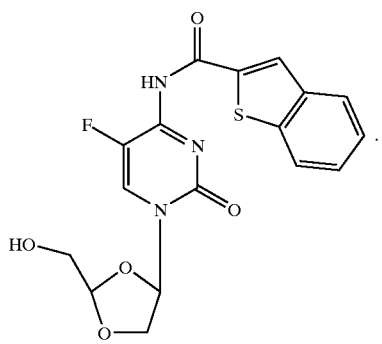

22. A pharmaceutical composition that includes an effective HIV or HBV treatment amount of a compound of claim 1 in a pharmaceutically acceptable carrier or diluent.

23. A pharmaceutical composition that includes an effective HIV or HBV treatment amount of a compound selected from the group consisting of β-D-N⁴-p-iodobenzoyl-5-fluorocytidine-1,3-dioxolane, β-D-N⁴-p-fluoro-benzoyl-5-fluorocytidine-1,3-dioxolane, β-D-N⁴-p-chlorobenzoyl-5-fluoro-cytidine-1,3-dioxolane, β-D-N⁴-p-bromobenzoyl-5-fluorocytidine-1,3-dioxolane, β-D-N⁴-p-ethyl-benzoyl-5-fluorocytidine-1,3-dioxolane, β-D-N⁴-p-t-butylbenzoyl-5-fluoro-cytidine-1,3-dioxolane.

24. A method for the treatment of a host infected with HIV that includes administering an effective amount of a compound of the formula:

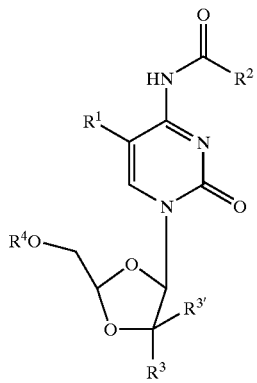

or a pharmaceutically acceptable salt thereof, wherein
iv) $R^1$ is chosen from hydrogen and halogen;
v) $R^2$ is chosen from alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen, CN, $CF_3$, $N_3$, $NO_2$, alkyl, haloalkyl, aminoalkyl, alkoxy, thioalkyl, alkenyl, alkynyl, and aryl;
vi) $R^3$ is chosen from H, halogen, CN, $CF_3$, $N_3$, $NO_2$, alkyl, alkenyl, and alkynyl;
vii) $R^{3'}$ is chosen from H, halogen methyl or ethyl; and
viii) $R^4$ is H, phosphate, carbonyl substituted with alkyl, alkenyl, alkynyl, aryl, sulfonate ester, a lipid, an amino acid, a peptide, or cholesterol,
in a pharmaceutically acceptable carrier.

25. A method for the treatment of a host infected with HBV that includes administering an effective amount of a compound of the formula:

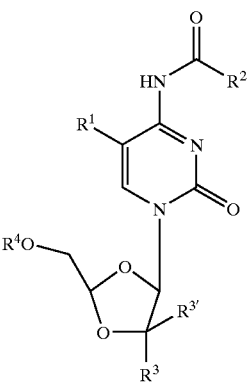

or a pharmaceutically acceptable salt thereof, wherein
ix) $R^1$ is chosen from hydrogen and halogen;
x) $R^2$ is chosen from alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen, CN, $CF_3$, $N_3$, $NO_2$, alkyl, haloalkyl, aminoalkyl, alkoxy, thioalkyl, alkenyl, alkynyl, and aryl;
xi) $R^3$ is chosen from H, halogen, CN, $CF_3$, $N_3$, $NO_2$, alkyl, alkenyl, and alkynyl;
xii) $R^{3'}$ is chosen from H, halogen methyl or ethyl; and
xiii) $R^4$ is H, phosphate, carbonyl substituted with alkyl, alkenyl, alkynyl, aryl, sulfonate ester, a lipid, an amino acid, a peptide, or cholesterol,
in a pharmaceutically acceptable carrier.

26. A method for the treatment of a host infected with HIV that includes administering an effective amount of a compound of the formula:

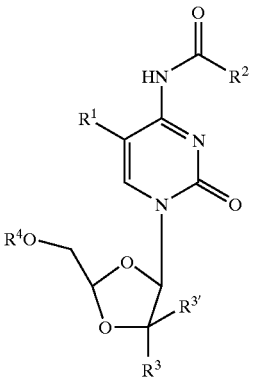

or a pharmaceutically acceptable salt thereof, wherein
xiv) $R^1$ is chosen from hydrogen and halogen;
xv) $R^2$ is chosen from alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen, CN, $CF_3$, $N_3$, $NO_2$, alkyl, haloalkyl, aminoalkyl, alkoxy, thioalkyl, alkenyl, alkynyl, and aryl;
xvi) $R^3$ is chosen from H, halogen, CN, $CF_3$, $N_3$, $NO_2$, alkyl, alkenyl, and alkynyl;
xvii) $R^{3'}$ is chosen from H, halogen, methyl or ethyl; and
xviii) $R^4$ is H, phosphate, carbonyl substituted with alkyl, alkenyl, alkynyl, aryl, sulfonate ester, a lipid, an amino acid, a peptide, or cholesterol, in a pharmaceutically acceptable carrier in combination with another anti-HIV agent.

27. A method for the treatment of a host infected with HBV that includes administering an effective amount of a compound of the formula:

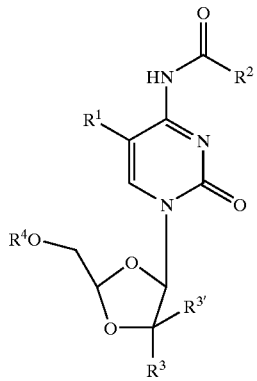

or a pharmaceutically acceptable salt thereof, wherein
xix) $R^1$ is chosen from hydrogen and halogen;
xx) $R^2$ is chosen from alkenyl, alkynyl, cycloalkyl, aminoalkyl, hydroxyalkyl, haloalkyl, thioalkyl, aryl, heteroaryl, and $C_6H_4R^6$ where $R^6$ is chosen from halogen, CN, $CF_3$, $N_3$, $NO_2$, alkyl, haloalkyl, aminoalkyl, alkoxy, thioalkyl, alkenyl, alkynyl, and aryl;
xxi) $R^3$ is chosen from H, halogen, CN, $CF_3$, $N_3$, $NO_2$, alkyl, alkenyl, and alkynyl;
xxii) $R^{3'}$ is chosen from H, halogen methyl or ethyl; and
xxiii) $R^4$ is H, phosphate, carbonyl substituted with alkyl, alkenyl, alkynyl, aryl, sulfonate ester, a lipid, an amino acid, a peptide, or cholesterol,
in a pharmaceutically acceptable carrier in combination with another anti-HIV agent.

28. The method of claims 24, 25, 26 or 27 wherein $R^1$ is fluorine.

29. The method of claims 24, 25, 26, or 27 wherein $R^3$ is fluorine and $R^{3'}$ is H.

30. A method for the treatment of a host infected with HIV that includes administering an effective amount of a compound selected from the group consisting of β-D-$N^4$-p-iodobenzoyl-5-fluorocytidine-1,3-dioxolane, β-D-$N^4$-p-fluoro-benzoyl-5-fluorocytidine-1,3-dioxolane, β-D-$N^4$-p-chlorobenzoyl-5-fluoro-cytidine-1,3-dioxolane, β-D-$N^4$-p-bromobenzoyl-5-fluorocytidine-1,3-dioxolane, β-D-$N^4$-p-ethyl-benzoyl-5-fluorocytidine-1,3-dioxolane, β-D-$N^4$-p-t-butylbenzoyl-5-fluoro-cytidine-1,3-dioxolane.

31. A method for the treatment of a host infected with HBV that includes administering an effective amount of a compound of one of claim 5 or 6–21 in a pharmaceutically acceptable carrier.

32. A method for the treatment of a host infected with HIV that includes administering an effective amount of a compound of one of claim 5 or 6–21 in a pharmaceutically acceptable carrier.

33. A method for the treatment of a host infected wit HIV that includes administering an effective amount of a compound of one of claim 5 or 6–21 in a pharmaceutically acceptable carrier in combination with another anti-HIV agent.

34. A method forte treatment of a host infected with HBV that includes administrating an effective amount of a compound of one of claim 5 or 6–21 in a pharmaceutically acceptable carrier in combination with another anti-HBV agent.

* * * * *